(12) United States Patent
Kimura

(10) Patent No.: US 8,450,070 B2
(45) Date of Patent: May 28, 2013

(54) METHOD FOR SCREENING OF CELL-PROTECTING AGENT

(75) Inventor: Haruhide Kimura, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/810,585

(22) PCT Filed: Dec. 26, 2008

(86) PCT No.: PCT/JP2008/073778
§ 371 (c)(1),
(2), (4) Date: Jun. 25, 2010

(87) PCT Pub. No.: WO2009/084653
PCT Pub. Date: Jul. 9, 2009

(65) Prior Publication Data
US 2010/0279311 A1    Nov. 4, 2010

(30) Foreign Application Priority Data

Dec. 28, 2007   (JP) .................................. 2007-339138

(51) Int. Cl.
*G01N 33/53*    (2006.01)
*G01N 33/567*   (2006.01)

(52) U.S. Cl.
USPC ............................. 435/7.1; 435/7.2; 435/7.21

(58) Field of Classification Search
None
See application file for complete search history.

(56) References Cited

FOREIGN PATENT DOCUMENTS

| WO | 2002/092606 | 11/2002 |
|---|---|---|
| WO | 2004/069999 | 8/2004 |

OTHER PUBLICATIONS

Supplementary European Search Report dated Dec. 17, 2010 in Application No. EP 08866880.1.
English translation of the International Preliminary Report on Patentability and Written Opinion, PCT/JP2008/073778, filed Dec. 26, 2008.
S. Ansar et al., "A Non-Toxic Hsp90 Inhibitor Protects Neurons from Aβ-Induced Toxicity", Bioorganic & Medicinal Chemistry Letters, vol. 17, No. 7, pp. 1984-1990, Apr. 1, 2007.
X. M. Yu et al., "Hsp90 Inhibitors Identified from a Library of Novobiocin Analogues", Journal of American Chemical Society, vol. 127, No. 37, pp. 12778-12779, Sep. 2005.
A. H. Salehi et al., "AEG3482 is an Antiapoptotic Compound that Inhibits Jun Kinase Activity and Cell Death Through Induced Expression of Heat Shock Protein 70", Chemistry & Biology, vol. 13, No. 2, pp. 213-223, Feb. 1, 2006.
K. A. Gallo et al., "Targeting HSSP90 to Halt Neurodegeneration", Chemistry & Biology, vol. 13, No. 2, pp. 115-116, Feb. 1, 2006.
H. Kimura et al., "ITZ-1, A Client-Selective Hsp90 Inhibitor, Efficiently Induces Heat Shock Factor 1 Activation", Chemistry & Biology, vol. 17, No. 1, pp. 18-27, Jan. 29, 2010.
International Search Report issued Feb. 10, 2010 in International (PCT) Application No. PCT/JP2008/073778.
Howard Doong, et al., "*CAIR-1/BAG-3 Abrogates Heat Shock Protein-70 Chaperone Complex-mediated Protein Degradation*", Accumulation of Poly-Ubiquitinated Hsp90 Client Proteins, J.Biol Chem, 2003, vol. 278, No. 31, pp. 28490-28500.
Mark Sisco et al., "*Reduced up-regulation of cytoprotective genes in rat cutaneous tissue during the second cycle of ischemia-reperfusion*", Wound Repair Regen, Mar. 2007, vol. 15, No. 2, pp. 203-212.
Chinfu San et al., "*Drug-Induced Heat Shock Protein and Protection of Hepatocytes*", Low Temperature Medicine, 2000, vol. 26, No. 1, pp. 5-9 (with English translation).
M. Dolores Lopez-Maderuelo et al., *Opposite effects of the Hsp90 inhibitor Geldanamycin: induction of apoptosis in PC12, and differentiation in N2A cells*, FEBS Lett, 2001, vol. 490, No. 1/2, pp. 23-27.
Soundara Raghavan Pavithra, et al., "*Recurrent Fever Promotes Plasmodium falciparum Development in Human Erythrocytes*", J.Biol chem., 2004, vol. 279, No. 45, pp. 46692-46699.
Swee Sharp et al., "*Inhibitors of the HSP90 molecular chaperon: current status*", Adv. Cancer Res. 2006; 95: 323-348.
Csaba Soti, et al.,"*Heat shock proteins as emerging therapeutic targets*", Br. J. Pharmacol. 2005; 146: 769-780.

*Primary Examiner* — Daniel E Kolker
*Assistant Examiner* — James Rogers
(74) *Attorney, Agent, or Firm* — Wenderoth, Lind & Ponack, L.L.P.

(57) ABSTRACT

The invention provides a screening method and screening kit for a cell protecting agent. Specifically, the invention provides a method for screening a cell protecting agent showing an Hsp90-binding activity and a heat shock protein expression-inducing activity but having no Hsp90 client protein degradation-promoting activity. The method comprises the following steps (1) to (3): (1) measuring the binding property of a test compound to Hsp90; (2) measuring the activity of a test compound to induce the expression of a heat shock protein, or measuring the activity of a test compound to disrupt an Hsp90/HSF-1 complex, by using a cell capable of expressing the heat shock protein; and (3) measuring the activity of a test compound to induce the degradation of an Hsp90 client protein by using a cell capable of expressing the Hsp90 client protein. The invention further provides specifically a kit for screening a cell protecting agent, comprising (1) Hsp90; (2) a reagent for measuring the heat shock protein expression-inducing activity; (3) an imidazothiazine derivative; and (4) a reagent for quantifying an Hsp90 client protein.

5 Claims, 3 Drawing Sheets

METHOD FOR SCREENING OF CELL-PROTECTING AGENT

This application is a U.S. National Stage of International Application No. PCT/JP2008/073778 filed Dec. 26, 2008.

TECHNICAL FIELD

The present invention relates to a method for screening a cell protecting agent, which is useful for various diseases such as heart diseases, neurological disorders, etc. and a kit therefor as well as a cell protecting agent obtained by the screening method.

BACKGROUND ART

Exposure of cells to stresses such as heat shock leads to the induction of a group of proteins called heat shock proteins (Hsp). Hsp plays a role in restoring the denatured proteins caused by various stresses such as heat shock stress, oxidative stress, etc. to their normal state in cells.

Hsp90 (heat shock protein 90), which is one of heat shock proteins, binds to various substrate proteins (client proteins) in vivo and regulates their functions. Hsp90 client proteins are known to include glucocorticoid receptor, Akt, cycline dependent kinase 4, etc. (cf., e.g., Non-Patent Document 1).

Hsp90 forms complexes with heat shock factor-1 (HSF-1) and maintains HSF-1 in an inactive state as the monomer to downregulate a heat shock reaction (cf., e.g., Non-Patent Document 2).

A substance that binds to Hsp90 to inhibit the activity (Hsp90 inhibitor) can induce the expression of heat shock proteins including Hsp70, and is thus expected to be used as a cell protecting agent which exhibits a cell protecting activity (cf., e.g., Patent Document 1 and Non-Patent Documents 1 and 3). The Hsp90 inhibitor can mediate the activation of HSF-1 to induce the expression of a heat shock protein such as Hsp70 having a cell protecting activity.

In various diseases such as heart diseases, neurological disorders, inflammatory disorders, etc., cell or tissue injury caused by oxidative stress or the like has become a problem. Cell protecting agents are considered to be promising drugs for the prevention/treatment of these diseases. Heat shock proteins including Hsp70 inhibit apoptosis induced by various factors such as ultraviolet exposure, active oxygen, etc. to exhibit therapeutic effects in disease model animals with heart diseases, neurodegenerative disorders, diabetes, etc. Accordingly, the Hsp90 inhibitor is a heat shock protein inducing compound and could be a preventive/therapeutic drug for the diseases described above. However, Hsp90 inhibitors such as geldanamycin cause the degradation of Hsp90 client proteins to generate cytotoxicity, and are unsatisfactory as cell protecting agents.

As a screening method to search for a Hsp90 inhibitor available as a cell protecting agent, there is a method for assaying the binding property of a test compound to Hsp90 (hereinafter "Hsp90 binding activity"). However, it cannot be determined merely by assaying the Hsp90 binding activity if a test compound would cause the degradation of Hsp90 client proteins to show cytotoxicity.

In view of the foregoing circumstances, a screening method has been sought to find an Hsp90 inhibitor having a minimal activity of promoting the degradation of an Hsp90 client protein and a minimal cytotoxicity and thus useful as a cell protecting agent.

Non-Patent Document 1: Heat shock proteins as emerging therapeutic targets, Br. J. Pharmacol., 2005; 146: p. 769-780

Non-Patent Document 2: Regulation of cellular functions by molecular chaperones, 132, 2001

Non-Patent Document 3: Inhibitors of the Hsp90 molecular chaperon: current status, Adv Cancer Res., 2006; 95:p. 323-348

Patent Document 1: International Publication No. WO 2004/069999

DISCLOSURE OF INVENTION

An object of the present invention is to provide a screening method and screening kit for a cell protecting agent, and so on.

The present inventors have found that an excellent cell protecting agent is obtained through a screening method, which comprises (1) measuring the binding property of a test compound to Hsp90, (2) measuring the activity of a test compound to induce the expression of a heat shock protein, and (3) measuring the activity of a test compound to induce the degradation of an Hsp90 client protein.

The present inventors have also found that an excellent cell protecting agent is obtained through the screening method, wherein the step (2) is measuring the activity of a test compound to disrupt an Hsp90/HSF-1 complex.

The present invention has been accomplished based on these findings. That is, the present invention is directed to the following items.

[1] A method for screening a cell protecting agent, which comprises (1) measuring the binding property of a test compound to Hsp90, (2) measuring the activity of a test compound to induce the expression of a heat shock protein, and (3) measuring the activity of a test compound to induce the degradation of an Hsp90 client protein.

[1a] A method for screening a cell protecting agent showing an Hsp90 binding activity and a heat shock protein expression-inducing activity but having no Hsp90 client protein degradation-promoting activity, which comprises (1) measuring the binding property of a test compound to Hsp90, (2) measuring the activity of a test compound to induce the expression of a heat shock protein and (3) measuring the activity of a test compound to induce the degradation of an Hsp90 client protein.

[1b] A method for screening a cell protecting agent which comprises performing the following steps (1) to (4) on a test compound: (1) measuring the binding property of a test compound to Hsp90, (2) measuring the activity of a test compound to induce the expression of a heat shock protein, (3) measuring the activity of a test compound to induce the degradation of an Hsp90 client protein and (4) screening a test compound showing the Hsp90 binding activity and the heat shock protein expression-inducing activity but having no Hsp90 client protein degradation-promoting activity.

[2] The screening method according to [1] above, wherein the step (1) comprises measuring the inhibitory activity of a test compound against the binding property of Hsp90 to an imidazothiazine derivative.

[2a] The screening method according to [2] above, wherein the step (1) comprises measuring and comparing (i) the binding level of an immobilized imidazothiazine derivative to Hsp90 in the absence of a test compound and (ii) the binding level of an immobilized imidazothiazine derivative to Hsp90 in the presence of a test compound.

[2b] The screening method according to [2a] above, wherein when the binding level of Hsp90 to the immobilized imidazothiazine derivative obtained in the presence of the test compound is less than that obtained in the absence of the test compound, the test compound is determined to have an inhibitory activity against the binding property of Hsp90 to the imidazothiazine derivative.

[2c] The screening method according to [2] above, wherein the step (1) comprises measuring and comparing (i) the binding level of immobilized Hsp90 to a labeled imidazothiazine derivative in the absence of the test compound and (ii) the binding level of immobilized Hsp90 to a labeled imidazothiazine derivative in the presence of the test compound

[2d] The screening method according to [2c] above, wherein when the binding level of immobilized Hsp90 to the labeled imidazothiazine obtained in the presence of the test compound is less than that obtained in the absence of the test compound, the test compound is determined to have an inhibitory activity against the binding property of Hsp90 to the imidazothiazine derivative.

[3] The screening method according to [1] above, wherein the step (2) comprises measuring the activity of a test compound to disrupt an Hsp90/HSF-1 complex.

[3a] The screening method according to [3] above, wherein when the protein level of the dissociated HSF-1 in the presence of a test compound is higher than that in the absence of a test compound, the test compound is determined to have the activity of disrupting the Hsp90/HSF-1 complex (namely, the heat shock protein expression-inducing activity).

[4] The screening method according to [1] above, wherein the step (3) comprises measuring the inhibitory activity of a test compound against the binding of Hsp90 to a client protein.

[5] The screening method according to [1] above, wherein the step (2) is measuring the activity of a test compound to induce the expression of a heat shock protein using a cell capable of expressing the heat shock protein.

[5a] The screening method according to [1] above, wherein the step (3) is measuring the activity of a test compound to induce the degradation of an Hsp90 client protein using a cell capable of expressing the Hsp90 client protein.

[5b] The screening method according to [1] above, wherein the step (2) is measuring the activity of a test compound to induce the expression of a heat shock protein using a cell capable of expressing the heat shock protein and the step (3) is measuring the activity of a test compound to induce the degradation of an Hsp90 client protein using a cell capable of expressing the Hsp90 client protein.

[5c] The screening method according to [5] or [5b] above, wherein the cell capable of expressing a heat shock protein is a human normal articular chondrocytes, the heat shock protein is Hsp70, and when the cell is incubated with the test compound and IL-1β, the test compound which increases the protein level of Hsp70 is determined to have the heat shock protein expression-inducing activity.

[6] The screening method according to [1] above, wherein the heat shock protein in the step (2) is at least one selected from the group consisting of Hsp40, Hsp70 and Hsp90.

[7] The screening method according to [1] above, wherein the Hsp90 client protein in the step (3) is at least one selected from the group consisting of a glucocorticoid receptor, Akt and cycline dependent kinase 4.

[8] The screening method according to [1] or [2] above, wherein the step (3) comprises measuring and comparing (i) the level of an Hsp90 client protein in a cell in the absence of the test compound and (ii) the level of an Hsp90 client protein in the cell in the presence of the test compound.

[8a] The screening method according to [1] or [2] above, wherein the step (3) comprises measuring the activity of a test compound to induce the degradation of an Hsp90 client protein using a cell capable of the expressing Hsp90 client protein, and further comprises measuring and comparing (i) the level of an Hsp90 client protein in the cell in the absence of the test compound and (ii) the level of an Hsp90 client protein in the cell in the presence of the test compound.

[8b] The screening method according to [8] above, wherein when there is no substantial difference in the protein levels measured in the absence of the test compound and in the presence of the test compound, the test compound is determined to have no client protein degradation-inducing activity.

[9] The screening method according to [8] above, wherein the level of the Hsp90 client protein is measured by western blotting using an antibody against the Hsp90 client protein.

[10] The screening method according to [1] above, wherein the cell protecting agent is an agent for the prevention/treatment of heart disease, neurological disease, brain disease, bone/joint disease, renal disease, liver disease or skin disease.

[10a] The screening method according to [1] above, wherein the cell protecting agent is an agent for the prevention/treatment of heart disease, neurological disease, brain disease, bone/joint disease, renal disease, liver disease, skin disease or metabolic disease.

[11] The screening method according to [1] above, which as the step (4) further comprises (4) screening a test compound showing the Hsp90 binding activity and the heat shock protein expression-inducing activity but having no Hsp90 client protein degradation-promoting activity.

[12] A kit for screening a cell protecting agent, comprising (1) Hsp90, (2) a reagent for quantification of a heat shock protein, (3) an imidazothiazine derivative and (4) a reagent for quantification of an Hsp90 client protein.

[12a] A kit for screening a cell protecting agent, comprising (1) Hsp90, (2) a reagent for measurement of the heat shock protein expression-inducing activity, (3) an imidazothiazine derivative and (4) a reagent for quantification of an Hsp90 client protein.

[12b] A kit for screening a cell protecting agent showing the Hsp90 binding activity and the heat shock protein expression-inducing activity but having no Hsp90 client protein degradation-promoting activity, comprising (1) Hsp90, (2) a reagent for quantification of a heat shock protein, (3) an imidazothiazine derivative and (4) a reagent for quantification of an Hsp90 client protein.

[13] A kit for screening a cell protecting agent, comprising (1) an Hsp90/HSF-1 complex, (2) Hsp90, (3) a reagent for quantification of Hsp90, (4) an imidazothiazine derivative and (5) a reagent for quantification of an Hsp90 client protein.

[13a] A kit for screening a cell protecting agent showing the Hsp90 binding activity and the heat shock protein expression-inducing activity but having no Hsp90 client protein degradation-promoting activity, comprising (1) an Hsp90/HSF-1 complex, (2) Hsp90, (3) a reagent for quantification of Hsp90, (4) an imidazothiazine derivative and (5) a reagent for quantification of an Hsp90 client protein.

[14] The screening kit according to [12] or [13] above, wherein the reagent for quantification of an Hsp90 client protein comprises an antibody against the Hsp90 client protein.

[15] The screening kit according to [12] or [13] above, wherein the Hsp90 client protein is at least one selected from the group consisting of a glucocorticoid receptor, Akt and cycline dependent kinase 4.

[16] The screening kit according to [12] above, wherein the heat shock protein in (2) is at least one selected from the group consisting of Hsp40, Hsp70 and Hsp90.

[17] A substance obtainable using the method according to [1] above or the kit according to [12] or [13] above, showing the Hsp90 binding activity and the heat shock protein expression-inducing activity, but having no Hsp90 client protein degradation-promoting activity.

[18] A cell protecting agent comprising the substance according to [17] above.

[19] A medicament comprising the substance according to [17] above.

[20] The medicament according to [19] above, which is an agent for the prevention/treatment of heart disease, neurological disease, brain disease, bone/joint disease, renal disease, liver disease or skin disease.

As is represented in EXAMPLES, the present invention provides a screening method to find such an excellent cell protecting agent having properties as the Hsp90 inhibitor, which has the activity of promoting the degradation of an Hsp90 client protein with a minimized cytotoxicity or no cytotoxicity. The present invention further provides a kit for screening the cell protecting agent described above.

According to the screening method of the present invention, "the cell protecting agent showing the Hsp90 binding activity and the heat shock protein expression-inducing activity and having minimized or no Hsp90 client protein degradation-promoting activity" or "the cell protecting agent showing the Hsp90 binding activity and the Hsp90/HSF-1 complex-disrupting activity and having minimized or no Hsp90 client protein degradation-promoting activity" can be readily acquired. These cell protecting agents do not cause the degradation of Hsp90 client proteins to minimize their cytotoxicity and are useful as agents for the prevention/treatment of various diseases.

BEST MODES FOR CARRYING OUT THE INVENTION

Method for Screening Cell Protecting Agent

Figure 1:
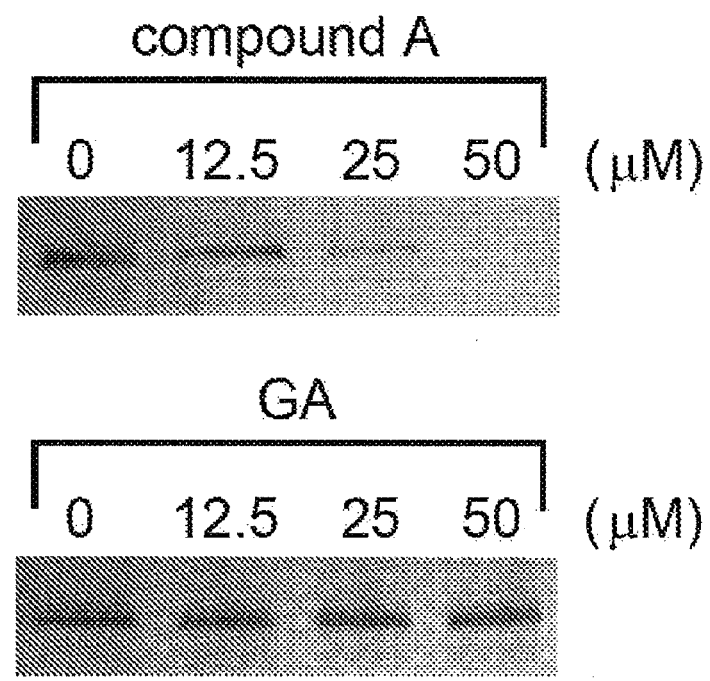
FIG. 1 is SDS-PAGE electrophoretograms showing the effects of a test compound (compound A) and a reference compound (geldanamycin: GA) on the binding of compound B-immobilized carrier to His-hHsp90α.

The present invention provides a method for screening a cell protecting agent which comprises (1) measuring the binding property of a test compound to Hsp90, (2) measuring the activity of a test compound to induce the expression of a heat shock protein, and (3) measuring the activity of a test compound to induce the degradation of an Hsp90 client protein. By applying the steps (1) to (3) described above to a test compound, an excellent cell protecting agent can be screened.

For the purpose of screening a test compound having the Hsp90 binding activity, a test compound is examined in the step (1) for the binding property of the test compound to Hsp90.

The step (1) comprises, for example, measuring an inhibitory activity of a test compound against the binding property of Hsp90 to an imidazothiazine derivative. The inhibitory activity of a test compound against the binding property of Hsp90 to an imidazothiazine derivative can be determined by measuring and comparing, for example, (i) the binding level of an immobilized imidazothiazine derivative to Hsp90 in the absence of the test compound and (ii) the binding level of an immobilized imidazothiazine derivative to Hsp90 in the presence of the test compound. Alternatively, the inhibitory activity can also be determined by measuring and comparing (i) the binding level of immobilized Hsp90 to a labeled imidazothiazine derivative in the absence of the test compound and (ii) the binding level of immobilized Hsp90 to a labeled imidazothiazine derivative in the presence of the test compound.

Hsp90 refers to heat shock protein 90 and is not particularly limited so long as the protein is capable of binding to imidazothiazine derivatives described later. The Hsp90 of the present invention further includes salts of the Hsp90 protein, modified Hsp90 protein, Hsp90 protein in which the amino acid sequence is partially modified in such a manner that is capable of binding to a carrier, and immobilized Hsp90 protein bound to a carrier. Examples of the carrier to be bound to the Hsp90 protein include insoluble polysaccharides such as agarose, dextran, cellulose, etc.; synthetic resins such as polystyrene, polyacrylamide, silicone, etc.; glass, and the like. Hsp90 may be bound to a carrier with known methods.

Hsp90 which may be employed are those derived from various animals, especially from human. As human Hsp90, human Hsp90α (GENBANK Accession No. P07900) and human Hsp90β (GENBANK Accession No. P08238) are preferred, more preferably, human Hsp90α tagged with histidine at the N terminus (e.g., His-hHsp90α, His2-hHsp90α, etc.). His-hHsp90α can be prepared as follows by a modification of the method described in, e.g., WO 2004/069999, pages 57-58, EXAMPLE 2(2).

First, the Hsp90α coding region in a human skeletal muscle complementary DNA (cDNA) library is amplified by polymerase chain reaction (PCR). The amplified human Hsp90α region is inserted into the cloning site of a plasmid vector to construct the His-hHsp90α expression vector. After the expression vector is transformed into *Escherichia coli*, the transformant is incubated to induce expression of the His-hHsp90α protein. After completion of the incubation, the recovered cells of *Escherichia coli* are suspended in a buffer (20 mM Tris-HCl (pH 7.9)/500 mM NaCl/5 mM imidazole) followed by ultrasonication. The cell lysate obtained is centrifuged and the supernatant is recovered. From the supernatant, the His-hHsp90α protein is obtained using a nickel column.

The imidazothiazine derivative is not particularly limited as far as it is a compound having an imidazothiazine skeleton and having the binding property to Hsp90. The imidazothiazine derivative of the present invention further includes an imidazothiazine derivative having a modified terminus capable of binding to a carrier, an immobilized imidazothiazine derivative bound to a carrier and a labeled imidazothiazine derivative. Examples of the carrier to be bound to the imidazothiazine derivative include insoluble polysaccharides such as agarose, dextran, cellulose, etc.; synthetic resins such as polystyrene, polyacrylamide, silicone, etc.; glass, and the like. The imidazothiazine derivative may be bound to a carrier with known methods.

The imidazothiazine derivative may be labeled using, for example, a radioactive isotope, a fluorescent dye or a luminescent substance.

Examples of the imidazothiazine derivative include the following compound (I) and salts thereof

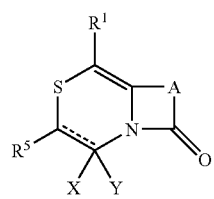

(I)

(wherein $R^1$ is $—(S)_n—R^2$ or $—NR^3R^4$; n is an integer of 0 to 2; $R^2$ is hydrogen atom or an optionally substituted hydrocarbon group or an optionally substituted heterocyclic group; $R^3$ and $R^4$, which may be the same or different, each represents hydrogen atom, an optionally substituted hydrocarbon group, an optionally substituted heterocyclic group, or a nitrogen-containing heterocyclic group formed by $R^3$ and $R^4$ taken together with the nitrogen atom bonded thereto, and $R^5$ represents hydrogen atom, an optionally substituted hydrocarbon group, cyano group or acyl group, an optionally esterified or amidated carboxyl group, or an optionally substituted heterocyclic group; wherein:

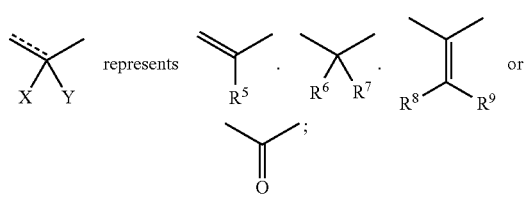

$R^6$ represents a hydrogen atom, an optionally substituted hydrocarbon group, cyano group or acyl group, an optionally esterified or amidated carboxyl group, or an optionally substituted heterocyclic group; $R^7$ represents an optionally substituted hydroxy group; each of $R^8$ and $R^9$ represents a hydrogen atom, or an optionally substituted hydrocarbon group ($R^5$ and $R^6$, $R^5$ and $R^8$ or $R^8$ and $R^9$ may be taken together to form an optionally substituted cyclic hydrocarbon or an optionally substituted heterocyclic group); wherein:

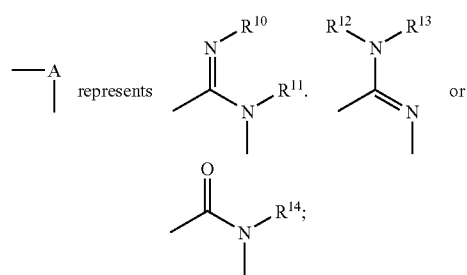

$R^{10}$ represents a hydrogen atom, $—ZR^{15}$ (wherein Z is $—SO_2—$, $—SO—$, $—CONR^{18}SO_2—$ (wherein $R^{18}$ is a $C_{1-6}$ alkyl), $—CONR^{19}—$ (wherein $R^{19}$ is a $C_{1-6}$ alkyl) or $—CO—$, $R^{15}$ is an optionally substituted hydrocarbon group, or an optionally substituted heterocyclic group) or $—P(O)R^{16}R^{17}$ (wherein each of $R^{16}$ and $R^{17}$ represents an optionally substituted hydrocarbon group, an optionally substituted hydroxy group, or an optionally substituted amino group); $R^{11}$ represents a hydrogen atom or an optionally substituted hydrocarbon group (wherein $R^{10}$ and $R^{11}$ may be taken together to form an optionally substituted nitrogen-containing heterocyclic group); each of $R^{12}$ and $R^{13}$ represents a hydrogen atom, an optionally substituted hydrocarbon group, or a nitrogen-containing heterocyclic group formed together with the nitrogen atom bonded thereto; and $R^{14}$ represents hydrogen atom, an optionally substituted hydrocarbon group, or $—ZR^{15}$ (wherein Z and $R^{15}$ have the same significance as defined above); provided that when $R^5$ represents a hydrogen atom,

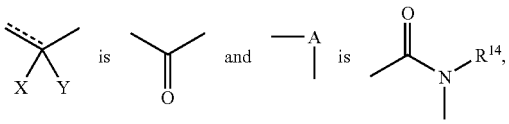

$R^{14}$ represents an optionally substituted hydrocarbon group or $-ZR^{15}$ (wherein Z and $R^{15}$ have the same significance as defined above)).

In the formula described above, $R^1$ represents $—(S)_n—R^2$ or $—NR^3R^4$; n represents an integer of 0 to 2; $R^2$ represents hydrogen atom, an optionally substituted hydrocarbon group, or an optionally substituted heterocyclic group; $R^3$ and $R^4$, which may be the same or different, each represents hydrogen atom, an optionally substituted hydrocarbon group, an optionally substituted heterocyclic group, or a nitrogen-containing heterocyclic group formed by $R^3$ and $R^4$ taken together with the nitrogen atom bonded thereto.

In the optionally substituted hydrocarbon group represented by $R^2$, the "hydrocarbon group" includes an alkyl, alkenyl, alkynyl, aryl, aralkyl, cycloalkyl and cycloalkenyl group, etc.

The "alkyl group" include a $C_{1-20}$ alkyl group (e.g., methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 3,3-dimethylbutyl, 1,3-dimethylbutyl, 2,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, isoheptyl, 1-methylhexyl, 2-methylhexyl, 3-methylhexyl, 4-methylhexyl, 1-ethylpentyl, 2-ethylpentyl, 3-ethylpentyl, 1-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 4,4-dimethylpentyl, 1,1,2-trimethylbutyl, 1,1,3-trimethylbutyl, 1,2,2-trimethylbutyl, 1,2,3-trimethylbutyl, 1,3,3-timethylbutyl, 2,2,3-trimethylbutyl, 2,3,3-trimethylbutyl, 1-ethyl-1-methylbutyl, 1-ethyl-2-methylbutyl, 1-ethyl-3-methylbutyl, 2-ethyl-1-methylbutyl, 2-ethyl-2-methylbutyl, 2-ethyl-3-methylbutyl, octyl, isooctyl, 1-methylheptyl, 2-methylheptyl, 3-methylheptyl, 4-methylheptyl, 5-methylheptyl, 1-ethylhexyl, 2-ethylhexyl, 3-ethylhexyl, 4-ethylhexyl, 1-propylpentyl, 2-propylpentyl, 1,1-dimethylhexyl, 2,2-dimethylhexyl, 3,3-dimethylhexyl, 4,4-dimethylhexyl, 5,5-dimethylhexyl, 3-ethyl-3-methylpentyl, 1,1-diethylbutyl, 2,2-diethylbutyl, 1,1,2,2-tetramethylbutyl, 1,1,3,3-tetramethylbutyl, 2,2,3,3-tetramethylbutyl, 1,1-dimethyl-2-ethylbutyl, nonyl, isononyl, 1-isobutyl-3-methylbutyl, decyl, isodecyl, undecyl, isoundecyl, dodecyl, isododecyl, tridecyl, isotridecyl, tetradecyl, isotetradecyl, pentadecyl, isopentadecyl, hexadecyl, isohexadecyl, heptadecyl, isoheptadecyl, octadecyl, isooctadecyl, nonadecyl, isononadecyl, etc.), preferably a $C_{1-10}$ alkyl group (e.g., methyl, ethyl, propyl, isopropyl, butyl, isobutyl, sec-butyl, tert-butyl, pentyl, isopentyl, 2-methylbutyl, hexyl, isohexyl, 2-ethylbutyl, 1,1-dimethylbutyl, 2,2-dimethylbutyl, 3,3-dimethylbutyl, heptyl, isoheptyl, 1-methylhexyl, 1-ethylpentyl, 3-ethylpentyl, 1-propylbutyl, octyl, isooctyl, 2-propylpentyl, nonyl, isononyl, 1-isobutyl-3-methylbutyl, decyl, isodecyl, etc.).

The "alkenyl group" includes a $C_{2-20}$ alkenyl group (e.g., vinyl, allyl, isopropenyl, 1-propenyl, 1-butenyl, 2-butenyl, 3-butenyl, 1,3-butadienyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1,3-pentadienyl, 2,4-pentadienyl, 1,4-pentadienyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1-ethyl-1-propenyl, 1-ethyl-2-propenyl, 1-hexenyl, 2-hexenyl, 3-hexenyl, 4-hexenyl, 5-hexenyl, 1,3-hexadienyl, 1,4-hexadienyl, 1,5-hexadienyl, 2,4-hexadienyl, 2,5-hexadienyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1-ethyl-1-butenyl, 2-ethyl-1-butenyl, 1-ethyl-2-butenyl, 2-ethyl-2-butenyl, 1-ethyl-3-butenyl, 2-ethyl-3-butenyl, 1-heptenyl, 2-heptenyl, 3-heptenyl, 4-heptenyl, 5-heptenyl, 6-heptenyl, 1,3-heptadienyl, 1,4-heptadienyl, 1,5-heptadienyl, 1,6-heptadienyl, 2,4-heptadienyl, 2,5-heptadienyl, 2,6-heptadienyl, 3,5-heptadienyl, 3,6-heptadienyl, 4,6-heptadienyl, 1-methyl-1-hexenyl, 1-methyl-2-hexenyl, 1-methyl-3-hexenyl, 1-methyl-4-hexenyl, 1-methyl-5-hexenyl, 2-methyl-1-hexenyl, 2-methyl-2-hexenyl, 2-methyl-3-hexenyl, 2-methyl-4-hexenyl, 2-methyl-5-hexenyl, 3-methyl-1-hexenyl, 3-methyl-2-hexenyl, 3-methyl-3-hexenyl, 3-methyl-4-hexenyl, 3-methyl-5-hexenyl, 4-methyl-1-hexenyl, 4-methyl-2-hexenyl, 4-methyl-3-hexenyl, 4-methyl-4-hexenyl, 4-methyl-5-hexenyl, 5-methyl-1-hexenyl, 5-methyl-2-hexenyl, 5-methyl-3-hexenyl, 5-methyl-4-hexenyl, 5-methyl-5-hexenyl, 1-methyl-2,4-hexadienyl, 2-methyl-2,4-hexadienyl, 3-methyl-2,4-hexadienyl, 4-methyl-2,4-hexadienyl, 5-methyl-2,4-hexadienyl, 5-methyl-2,5-hexadienyl, 1-ethyl-1-pentenyl, 2-ethyl-1-pentenyl, 3-ethyl-1-pentenyl, 1-ethyl-2-pentenyl, 2-ethyl-2-pentenyl, 3-ethyl-2-pentenyl, 1-ethyl-3-pentenyl, 2-ethyl-3-pentenyl, 3-ethyl-3-pentenyl, 1-ethyl-4-pentenyl, 2-ethyl-4-pentenyl, 3-ethyl-4-pentenyl, 1-propyl-1-butenyl, 1-propyl-2-butenyl, 1-propyl-3-butenyl, 2-octenyl, 3-octenyl, 4-octenyl, 5-octenyl, 6-octenyl, 7-octenyl, 1-methyl-2-heptenyl, 1-methyl-3-heptenyl, 1-methyl-4-heptenyl, 1-methyl-5-heptenyl, 1-methyl-6-heptenyl, 6-methyl-2-heptenyl, 6-methyl-3-heptenyl, 6-methyl-4-heptenyl, 6-methyl-5-heptenyl, 6-methyl-6-heptenyl, 6-methyl-3,5-heptadienyl, 6-methyl-2,5-heptadienyl, 4-ethyl-2-hexenyl, 4-ethyl-3-hexenyl, 2-nonenyl, 8-nonenyl, 7-methyl-1-octenyl, 7-methyl-2-octenyl, 7-methyl-3-octenyl, 7-methyl-4-octenyl, 7-methyl-5-octenyl, 7-methyl-6-octenyl, 7-methyl-7-octenyl, 1-ethyl-2-heptenyl, 1-ethyl-3-heptenyl, 1-ethyl-4-heptenyl, 1-ethyl-5-heptenyl, 1-ethyl-6-heptenyl, 5-ethyl-2-heptenyl, 5-ethyl-3-heptenyl, 5-ethyl-4-heptenyl, 5-ethyl-5-heptenyl, 5-ethyl-6-heptenyl, 2-decenyl, 9-decenyl, 8-methyl-2-nonenyl, 8-methyl-3-nonenyl, 8-methyl-4-nonenyl, 8-methyl-5-nonenyl, 8-methyl-6-nonenyl, 8-methyl-7-nonenyl, 8-methyl-8-nonenyl, 3,7-dimethyl-2,6-octadienyl, 2-undecenyl, 10-undecenyl, 9-methyl-2-decenyl, 9-methyl-8-decenyl, 9-methyl-9-decenyl, 2-dodecenyl, 11-dodecenyl, 10-methyl-2-undecenyl, 10-methyl-9-undecenyl, 10-methyl-10-undecenyl, 2-tridecenyl, 12-tridecenyl, 11-methyl-2-dodecenyl, 11-methyl-10-dodecenyl, 1'-methyl-1'-dodecenyl, 2-tetradecenyl, 13-tetradecenyl, 12-methyl-2-tridecenyl, 12-methyl-11-tridecenyl, 12-methyl-12-tridecenyl, 2-pentadecenyl, 14-pentadecenyl, 13-methyl-2-tetradecenyl, 13-methyl-12-tetradecenyl, 13-methyl-13-tetradecenyl, 3,7,11-trimethyl-2,6,10-dodecatrienyl, 2-hexadecenyl, 15-hexadecenyl, 14-methyl-2-pentadecenyl, 14-methyl-13-pentadecenyl, 14-methyl-14-pentadecenyl, 2-heptadecenyl, 16-heptadecenyl, 15-methyl-2-hexadecenyl, 15-methyl-14-hexadecenyl, 15-methyl-15-hexadecenyl, 2-octadecenyl, 17-octadecenyl, 9,12-octadecadienyl, 9,12, 15-octadecatrienyl, 9,11,13-octadecatrienyl, 16-methyl-2-heptadecenyl, 16-methyl-15-heptadecenyl, 16-methyl-16-heptadecenyl, 2-nonadecenyl, 18-nonadecenyl, 17-methyl-2-octadecenyl, 17-methyl-16-octadecenyl, 17-methyl-17-octadecenyl, 2-eicosenyl, 19-eicosenyl, 5,8,11,14-icosatetraenyl, 18-methyl-2-nonadecenyl, 18-methyl-17-nonadecenyl, 18-methyl-18-nonadecenyl, 3,7,11,15-tetramethyl-2,6,10,14-dodecatetraenyl, etc.), preferably a $C_{2-10}$ alkenyl group (e.g., vinyl, allyl, isopropenyl, 2-methyl-1-propenyl, 3-butenyl, 4-pentenyl, 3-methyl-2-butenyl, 3-methyl-3-butenyl, 5-hexenyl, 4-methyl-2-pentenyl, 4-methyl-3-pentenyl, 4-methyl-4-pentenyl, 6-heptenyl, 5-methyl-2-hexenyl, 5-methyl-3-hexenyl, 5-methyl-4-hexenyl, 5-methyl-5-hexenyl, 5-methyl-2,4-hexadienyl, 7-octenyl, 6-methyl-2-heptenyl, 6-methyl-3-heptenyl, 6-methyl-4-heptenyl, 6-methyl-5-heptenyl, 6-methyl-6-heptenyl, 8-nonenyl, 9-decenyl, 3,7-dimethyl-2,6-octadienyl, etc.).

The "alkynyl" group includes a $C_{2-20}$ alkynyl group (e.g., ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-3-butynyl, 2-methyl-3-butynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 2-octynyl, 3-octynyl, 4-octynyl, 5-octynyl, 6-octynyl, 7-octynyl, 2-nonynyl, 8-nonynyl, 2-decynyl, 9-decynyl, 2-undecynyl, 10-undecynyl, 2-dodecynyl, 11-dodecynyl, 2-tridecynyl, 12-tridecynyl, 2-tetradecynyl, 13-tetradecynyl, 2-pentadecynyl, 14-pentadecynyl, 2-hexadecynyl, 15-hexadecynyl, 2-heptadecynyl, 16-heptadecynyl, 2-octadecynyl, 17-octadecynyl, 2-nonadecynyl, 18-nonadecynyl, 2-eicosynyl, 19-eicosynyl, etc.), preferably a $C_{2-8}$ alkenyl group (e.g., ethynyl, 1-propynyl, 2-propynyl, 2-butynyl, 3-butynyl, 2-pentynyl, 4-pentynyl, 2-hexynyl, 5-hexynyl, 2-heptynyl, 6-heptynyl, 2-octynyl, 7-octynyl, etc.).

The "aryl group" includes a $C_{6-10}$ aryl group (e.g., phenyl, o-tolyl, m-tolyl, p-tolyl, 2-, 3- or 4-biphenyl, 1- or 2-naphthyl, anthryl, phenanthryl, etc.), preferably phenyl, p-tolyl, 2-, 3- or 4-biphenyl, 1- or 2-naphthyl, etc.

The "aralkyl group" includes a $C_{7-10}$ aralkyl group (e.g., benzyl, 1-phenethyl, 2-phenethyl, 1-methyl-2-phenethyl, 1-methyl-1-phenethyl, 1,1-dimethyl-2-phenethyl, 1-phenylpropyl, 2-phenylpropyl, 3-phenylpropyl, 1-methyl-2-phenylpropyl, 2-methyl-2-phenylpropyl, 1-phenylbutyl, 2-phenylbutyl, 3-phenylbutyl, 4-phenylbutyl, 1-phenylpentyl, 2-phenylpentyl, 3-phenylpentyl, 4-phenylpentyl, 5-phenylpentyl, 3-methyl-3-phenylbutyl, 1,1-dimethyl-3-phenylpropyl, 2,2-dimethyl-3-phenylpropyl, 1,1-dimethyl-4-phenylbutyl, 2,2-dimethyl-4-phenylbutyl, 3,3-dimethyl-4- phenylbutyl, 4-methyl-4-phenylpentyl, 1-methyl-5-phenylpentyl, 2-methyl-5-phenylpentyl, 3-methyl-5-phenylpentyl, 4-methyl-5-phenylpentyl, 1-naphthylmethyl, 2-naphthylmethyl, 1-naphthylethyl, 2-naphthylethyl, 2-biphenylmethyl, 3-biphenylmethyl, 4-biphenylmethyl, 1-anthrylmethyl, 2-anthrylmethyl, 9-anthrylmethyl, phenanthrylmethyl, etc.), preferably benzyl, 2-phenethyl, 2-phenylpropyl, 3-phenylpropyl, 2-methyl-2-phenylpropyl, 4-phenylbutyl, 1-naphthylmethyl, 2-naphthylmethyl, 1-naphthylethyl, 2-naphthylethyl, 2-biphenylmethyl, 3-biphenylmethyl, 4-biphenylmethyl, and the like.

The "cycloalkyl group" includes a $C_{3-8}$ cycloalkyl group (e.g., cyclopropyl, cyclobutyl, cyclopentyl, cyclohexyl, cycloheptyl, cyclooctyl, etc.). Furthermore, an aryl group such as phenyl, etc. may be fused to the cycloalkyl group, and examples include indanyl, benzocyclohexyl, benzocycloheptyl, benzocyclooctyl, and the like. Among others, cyclohexyl, cycloheptyl, cyclooctyl, indanyl, benzocycloheptyl and the like are preferred.

This cycloalkyl group may be bridged via a linear atomic chain having 1 or 2 carbon atoms to form a bridged cyclic hydrocarbon residue such as bicyclo[2.2.1]heptyl, bicyclo[2.2.2]octyl, bicyclo[3.2.1]octyl, bicyclo[3.3.1]nonyl, bicyclo[3.2.2]nonyl, etc. (preferably, cyclohexyl bridged via a linear atomic chain having 1 to 2 carbon atoms, and more preferably, bicyclo[2.2.1]heptyl, etc.). The cycloalkyl group may also form an adamantyl group.

The "cycloalkenyl group" includes a $C_{3-8}$ cycloalkenyl group (e.g., 2-cyclopropenyl, 2-cyclobutenyl, 2-cyclopentenyl, 3-cyclopentenyl, 2-cyclohexenyl, 3-cyclohexenyl, 2-cycloheptenyl, 3-cycloheptenyl, 4-cycloheptenyl, 2-cyclooctenyl, 3-cyclooctenyl and 4-cyclooctenyl. An aryl group such as phenyl, etc. may also be fused to the cycloalkenyl group and examples include indenyl, benzocyclohexenyl, benzocycloheptenyl, benzocyclooctenyl, and the like. Among others, 2-cyclohexenyl, 2-cycloheptenyl, cyclooctyl and indenyl are preferred.

In the "optionally substituted hydrocarbon group" represented by $R^2$, the substituent includes, for example, (1) nitro, (2) oxo, (3) a halogen atom (e.g., fluorine, chlorine, bromine and iodine), (4) cyano, (5) methylene, (6) an optionally substituted lower alkyl group, (7) an optionally substituted lower alkenyl group, (8) an optionally substituted lower alkynyl group, (9) an optionally substituted aryl group, (10) an optionally substituted aralkyl group, (11) an optionally substituted cycloalkyl group, (12) a lower haloalkyl group, (13) an optionally esterified or amidated carboxyl group, (14) thiocarbamoyl, (15) an acyl group, (16) amidyl, (17) an optionally substituted hydroxy group, (18) an optionally substituted sulfanyl group, (19) an optionally substituted alkylsulfonyl group, (20) an optionally substituted arylsulfinyl group, (21) an optionally substituted alkylsulfonyl group, (22) an optionally substituted arylsulfonyl group, (23) an optionally esterified or amidated sulfonyl acid group, (24) an optionally substituted amino group, (25) a guanidyl group which may optionally be substituted with nitro group, (26) an optionally substituted heterocyclic group, (27) an alkylenedioxy group, (28) imino, (29) an optionally substituted cycloalkenyl group, and the like. The hydrocarbon group may have 1 to 6 substituents selected from these substituents at a substitutable position(s).

In the "optionally substituted lower alkyl group" as the substituent in the "optionally substituted hydrocarbon group" represented by $R^2$, the "lower alkyl group" includes, for example, a $C_{1-4}$ alkyl group such as methyl, ethyl, n-propyl, isopropyl, butyl, isobutyl, sec-butyl, tert-butyl, and the like.

The substituents which the "lower alkyl group" may optionally have include, for example, (1) nitro, (2) oxo, (3) a halogen atom (e.g., fluorine, chloride, bromine, etc.), (4) cyano, (5) methylene, (6) a lower alkyl group (e.g., a $C_{1-4}$ alkyl group such as methyl, ethyl, n-propyl, isopropyl, butyl, isobutyl, sec-butyl, tert-butyl, etc.), (7) a lower alkenyl group (e.g., a $C_{2-5}$ alkenyl group such as vinyl, allyl, isopropenyl, 1-butenyl, 2-butenyl, 3-methyl-2-butenyl, 3-methyl-3-butenyl, 1-pentenyl, 2-pentenyl, etc.), (8) a lower alkynyl group (a $C_{2-5}$ alkynyl group such as ethynyl, propargyl, 2-butynyl, 2-pentynyl, etc.), (9) an aryl group (e.g., a $C_{2-12}$ aryl group such as phenyl, 2-, 3- or 4-tolyl, 1- or 2-naphthyl, 2-, 3- or 4-biphenyl, etc.), (10) an aralkyl group (e.g., a $C_{7-13}$ aralkyl group such as benzyl, 2-phenethyl, 3-phenylpropyl, 1- or 2-naphthylmethyl, 2-, 3- or 4-biphenylmethyl, etc.), (11) a cycloalkyl group (e.g., a $C_{3-8}$ cycloalkyl group such as cyclopropyl, cyclobutyl, cyclopentyl, cyclohexyl, cycloheptyl, cyclooctyl, etc.), (12) an optionally esterified or amidated carboxyl group (e.g., carboxyl, a $C_{2-18}$ alkoxycarbonyl group (e.g., methoxycarbonyl, ethoxycarbonyl, propoxycarbonyl, tert-butoxycarbonyl, hexyloxycarbonyl, dodecyloxycarbonyl, hexadecyloxycarbonyl, etc.), a $C_{2-18}$ alkenyloxycarbonyl group (e.g., allyloxycarbonyl, octa-2,6-dienyloxycarbonyl, dodeca-2,6,10-trienyloxycarbonyl, etc.), an aryloxycarbonyl group (e.g., phenoxycarbonyl, 1-naphthoxycarbonyl, 2-naphthoxycarbonyl, etc.), an aralkyloxycarbonyl group (e.g., benzyloxycarbonyl, phenethyloxycarbonyl, 3-phenylpropoxycarbonyl, etc.), carbamoyl, an N-monosubstituted carbamoyl group substituted with the lower alkyl group, lower alkenyl group, cycloalkyl group, aryl group, aralkyl group or heterocyclic group (which is the same as the "optionally substituted heterocyclic group" as the substituent for the "optionally substituted hydrocarbon group" represented by $R^2$ later described) described above, an N,N-disubstituted carbamoyl group substituted with the lower alkyl group, lower alkenyl group, cycloalkyl group, aryl group, aralkyl group or heterocyclic group (which is the same as the "optionally substituted heterocyclic group" as the substituent for the "optionally substituted hydrocarbon group" represented by $R^2$ later described) described above, a cyclic aminocarbamoyl group (e.g., N-pyrrolidylcarbonyl, N-imidazolylcarbonyl, N-piperidylcarbonyl, N-piperazylcarbonyl, N-methyl-N'-piperazylcarbonyl, N-morpholylcarbonyl, etc.)), (13) an optionally substituted hydroxy group (e.g., a hydroxy group which may optionally be substituted with the lower alkyl group, lower alkenyl group, cycloalkyl group, aryl group, aralkyl group or optionally esterified or amidated carboxyl group described above, an alkylsulfanylthiocarbonyloxy group (e.g., methylsulfanylthiocarbonyloxy, ethylsulfanylthiocarbonyloxy, tert-butoxysulfanylthiocarbonyloxy, etc.), an aralkylsulfanylthiocarbonyloxy group (e.g., benzylsulfanylthiocarbonyloxy, etc.), an N-imidazolylthiocarbonyloxy group, an N-morpholylthiocarbonyloxy group, etc., (14) an optionally substituted sulfanyl group (e.g., sulfanyl, an alkylsulfanyl group (e.g., methylsulfanyl, ethylsulfanyl, isopropylsulfanyl, tert-butylsulfanyl, etc.), an arylsulfonyl group (e.g., phenylsulfanyl, etc.), an aralkylsulfanyl group (e.g., benzylsulfanyl, etc.), etc., (15) an alkylsulfonyl group (e.g., methylsulfonyl, ethylsulfonyl, isopropylsulfonyl, butylsulfonyl, etc.), (16) an arylsulfonyl group (e.g., benzenesulfinyl, toluenesulfinyl, etc.), (17) an optionally substituted amino group (e.g., a mono- or di-substituted amino group substituted with an amino, alkyl or aralkyl group (e.g., methylamino, ethylamino, isopropylamino, dimethylamino, diethylamino, ethylmethylamino, benzylamino, benzylmethylamino, etc.), an acylamino (e.g., formylamino, acetylamino, propionylamino, butyrylamino, isobutyrylamino, valerylamino, isovalerylamino, pivaloylamino, benzoylamino, phenacylamino, etc.), an alkoxycarbonylamino (e.g., methoxycarbonylamino, ethoxycarbonylamino, tert-butoxycarbonylamino, etc.), an aryloxycarbonylamino (e.g., phenoxycarbonylamino, naphthyloxycarbonylamino, etc.), an aralkyloxycarbonylamino (e.g., benzyloxycarbonylamino, phenethyloxycarbonylamino, etc.), an alkylsulfonylamino (e.g., methylsulfonylamino, ethylsulfonylamino, isopropylsulfonylamino, butylsulfonylamino, etc.), an arylsulfonylamino (e.g., benzenesulfonylamino, naphthylsulfonylamino, etc.), etc.), (18) an alkylenedioxy group (e.g., methylenedioxy, ethylenedioxy, etc.), (19) imino, and the like. The hydrocarbon group may optionally have 1 to 4 substituents selected from those described above at a substitutable position(s).

In the "optionally substituted lower alkenyl group" as the substituent for the "optionally substituted hydrocarbon" represented by $R^2$, the "lower alkenyl group" includes, for example, a $C_{2-5}$ alkenyl group such as vinyl, allyl, isopropenyl, 1-butenyl, 2-butenyl, 3-methyl-2-butenyl, 3-methyl-3-butenyl, 1-pentenyl, 2-pentenyl, etc. The substituent which the "lower alkenyl group" may optionally have includes a substituent whose type and quantity are the same as those described above for the "optionally substituted lower alkyl group" as the substituent in the "optionally substituted hydrocarbon group" represented by $R^2$.

In the "optionally substituted lower alkynyl" as the substituent for "optionally substituted hydrocarbon group" represented by $R^2$, the "lower alkynyl group" includes, for example, a $C_{2-5}$ alkyl group such as a lower alkynyl group, e.g., ethynyl, propargyl, 2-butynyl, 2-pentynyl, etc. The substituent which the "lower alkynyl group" may optionally have includes a substituent whose type and quantity are the same as those described above for the "optionally substituted lower alkyl group" as the substituent in the "optionally substituted hydrocarbon group" represented by $R^2$.

In the "optionally substituted aryl group" as the substituent for the "optionally substituted hydrocarbon group" represented by $R^2$, the "aryl group" includes, for example, a $C_{2-12}$ aryl group such as phenyl, 2-, 3- or 4-tolyl, 1- or 2-naphthyl, 2-, 3- or 4-biphenyl, and the like. The substituent which the "aryl group" may optionally have includes a substituent whose type and quantity are the same as those described above for the "optionally substituted lower alkyl group" as the substituent in the "optionally substituted hydrocarbon group" represented by $R^2$.

In the "optionally substituted aralkyl group" as the substituent for "the optionally substituted hydrocarbon group" represented by $R^2$, the "aralkyl group" includes, for example, a $C_{7-13}$ aralkyl group such as benzyl, 2-phenethyl, 3-phenylpropyl, 1- or 2-naphthylmethyl, 2-, 3- or 4-biphenylmethyl, and the like. The substituent which the "aralkyl group" may optionally have includes a substituent whose type and quantity are the same as those described above for the "optionally substituted lower alkyl group" as the substituent in the "optionally substituted hydrocarbon group" represented by $R^2$.

In the "optionally substituted cycloalkyl group" as the substituent for "the optionally substituted hydrocarbon group" represented by $R^2$, the "cycloalkyl group" includes, for example, a $C_{3-8}$ cycloalkyl group such as cyclopropyl, cyclobutyl, cyclopentyl, cyclohexyl, cycloheptyl, cyclooctyl, etc., bicyclo[2.2.1]heptyl, bicyclo[2.2.2]octyl, bicyclo[3.2.1]octyl, bicyclo[3.3.1]nonyl, bicyclo[3.2.2]nonyl and adamantyl. The substituent which the "cycloalkyl group" may optionally have includes a substituent whose type and quantity are the same as those described above for the "optionally substituted lower alkyl group" as the substituent in the "optionally substituted hydrocarbon group" represented by $R^2$.

The "lower haloalkyl group" as the substituent for the "optionally substituted hydrocarbon group" represented by $R^2$ includes, for example, a lower alkyl group substituted with 1 to 6 halogen groups such as fluoromethyl, difluoromethyl, trifluoromethyl, 2-fluoroethyl, 2,2-difluoroethyl, 2,2,2-trifluoroethyl, 1,1,2,2-tetrafluoroethyl, 1,1,2,2,2-pentafluoroethyl, 3-fluoropropyl, 3,3-difluoropropyl, 3,3,3-trifluoropropyl, 2,2,3,3,3-pentafluoropropyl, 4-fluorobutyl, 4,4-difluorobutyl, 4,4,4-trifluorobutyl, 3,3,4,4,4-pentafluorobutyl, 5-fluoropentyl, 5,5-difluoropentyl, 5,5,5-trifluoropentyl, 4,4,5,5,5-pentafluoropentyl, chloromethyl, dichloromethyl, bromomethyl, and the like.

The "optionally esterified or amidated carboxyl group" as the substituent for "the optionally substituted hydrocarbon group" represented by $R^2$ includes carboxyl, an alkoxycarbonyl group, an alkenyloxycarbonyl group, an aryloxycarbonyl group, an aralkyloxycarbonyl group, carbamoyl, an N-monosubstituted carbamoyl group, and an N,N-disubstituted carbamoyl group.

The "alkoxycarbonyl group" includes, for example, a $C_{2-18}$ alkoxycarbonyl group such as methoxycarbonyl, ethoxycarbonyl, propoxycarbonyl, tert-butoxycarbonyl, hexyloxycarbonyl, dodecyloxycarbonyl, hexadecyloxycarbonyl, etc. The "alkoxycarbonyl group" may optionally have a substituent, including a substituent whose type and quantity are the same as those described above for the "optionally substituted lower alkyl group" as the substituent in the "optionally substituted hydrocarbon group" represented by $R^2$.

The "alkenyloxycarbonyl group" includes, for example, a $C_{2-18}$ alkenyloxycarbonyl group such as allyloxycarbonyl, octa-2,6-dienyloxycarbonyl, dodeca-2,6,10-trienyloxycarbonyl, etc. The "alkenyloxycarbonyl group" may optionally have a substituent, including a substituent whose type and quantity are the same as those described above for the "optionally substituted lower alkyl group" as the substituent in the "optionally substituted hydrocarbon group" represented by $R^2$.

The "aryloxycarbonyl group" includes, for example, phenoxycarbonyl, 1-naphthoxycarbonyl, 2-naphthoxycarbonyl, etc. The "aryloxycarbonyl group" may optionally have a substituent, including a substituent whose type and quantity are the same as those described above for the "optionally substituted lower alkyl group" as the substituent in the "optionally substituted hydrocarbon group" represented by $R^2$.

The "aralkyloxycarbonyl group" includes, for example, an aralkyloxycarbonyl group such as benzyloxycarbonyl, phenethyloxycarbonyl, 3-phenylpropoxycarbonyl, etc. The "aralkyloxycarbonyl group" may optionally have a substituent, including a substituent whose type and quantity are the same as those described above for "optionally substituted lower alkyl group" as the substituent in the "optionally substituted hydrocarbon group" represented by $R^2$.

The substituents for the "N-monosubstituted carbamoyl group" include, for example, a lower alkyl (e.g., methyl, ethyl, propyl, isopropyl, butyl, isobutyl, tert-butyl, pentyl, hexyl, etc.), a lower alkenyl (e.g., vinyl, allyl, isopropenyl, propenyl, butenyl, pentenyl, hexenyl, etc.), a cycloalkyl (e.g., cyclopropyl, cyclobutyl, cyclopentyl, cyclohexyl, etc.), an aryl (e.g., phenyl, 1-naphthyl, 2-naphthyl), an aralkyl (e.g., benzyl, phenethyl, etc.), a heterocyclic group (for example, the same substituents as the "optionally substituted heterocyclic group" as the substituent described below for the "optionally substituted hydrocarbon group" represented by $R^2$, and the like. The lower alkyl, lower alkenyl, cycloalkyl, aryl, aralkyl and heterocyclic group described above may optionally have a substituent, including a substituent whose type and quantity are the same as those described above for the "optionally substituted lower alkyl group" as the substituent in the "optionally substituted hydrocarbon group" represented by $R^2$.

The substituent of the "N,N-disubstituted carbamoyl group" refers to a carbamoyl group having 2 substituents on the nitrogen atom and includes the same substituents as those described above for the "N-monosubstituted carbamoyl group". In some case, the two substituents may be taken together with the nitrogen atom to form a cyclic amino. In this case, the cyclic aminocarbamoyl includes, for example, N-pyrrolidylcarbonyl, N-imidazolylcarbonyl, N-piperidylcarbonyl, N-piperazylcarbonyl, N-methyl-N'-piperazylcarbonyl, N-morpholylcarbonyl, and the like.

The "acyl group" as the substituent for the "optionally substituted hydrocarbon group" represented by $R^2$ includes a group formed by bonding a carbonyl and a substituent having a hydrogen atom or an "N-monosubstituted carbamoyl group" described above on the nitrogen atom. The acyl group includes, for example, a lower alkanoyl group such as formyl, acetyl, propionyl, etc., an aroyl group such as benzoyl, naphthoyl, etc.

The substituents for the "optionally substituted hydroxy group" as the substituent for the "optionally substituted hydrocarbon group" represented by $R^2$ include an optionally substituted lower alkyl group, an optionally substituted lower alkenyl group, an optionally substituted lower alkynyl group, an optionally substituted aryl group, an optionally substituted aralkyl group, an optionally substituted cycloalkyl group, an esterified or amidated carboxyl group, an optionally substituted alkylsulfanylthiocarbonyl group, an optionally substituted aralkylsulfanylthiocarbonyl group, an optionally substituted alkylsulfonyl group, an optionally substituted arylsulfonyl group, an optionally substituted N-imidazolylthiocarbonyl, an optionally substituted N-morpholylthiocarbonyl, a protecting group for hydroxy, and the like. The "optionally substituted lower alkyl group," "optionally substituted lower alkenyl group," "optionally substituted lower alkynyl group," "optionally substituted aryl group," "optionally substituted aralkyl group" and "optionally substituted cycloalkyl group" described above include the same as the "optionally substituted lower alkyl group," "optionally substituted lower alkenyl group," "optionally substituted lower alkynyl group," "optionally substituted aryl group," "optionally substituted aralkyl group" and "optionally substituted cycloalkyl group" as the substituent described above for the "optionally substituted hydrocarbon group" represented by $R^2$. The "esterified or amidated carboxyl group" includes a group formed by removing carboxyl from the "optionally esterified or amidated carboxyl group" as the substituent described above for the "optionally substituted hydrocarbon group" represented by $R^2$. The "optionally substituted alkylsulfanylthiocarbonyl group" includes, for example, methylsulfanylthiocarbonyl, ethylsulfanylthiocarbonyl, tert-butoxysulfanylthiocarbonyl, etc. The "optionally substituted aralkylsulfanylthiocarbonyl group" includes benzylsulfanylthiocarbonyloxy, and the like. The "optionally substituted alkylsulfonyl group" includes methylsulfonyl, ethylsulfonyl, isopropylsulfonyl, butylsulfonyl, etc. The "optionally substituted arylsulfonyl group" includes benzenesulfonyl, p-toluenesulfonyl, m-toluenesulfonyl, o-toluenesulfonyl, etc. The substituent, which the "optionally substituted alkylsulfanylthiocarbonyl group", "optionally substituted aralkylsulfanylthiocarbonyl group", "optionally substituted alkylsulfonyl group" and "optionally substituted arylsulfonyl group" may optionally have, includes a substituent whose type and quantity are the same as those described above for the "optionally substituted lower alkyl group" as the substituent for the "optionally substituted hydrocarbon group" represented by $R^2$. The substituent for the "optionally substituted N-imidazolylthiocarbonyl" and the "optionally substituted N-morpholylthiocarbonyl group" includes a substituent whose type and quantity are the same as those described above for the "optionally substituted lower alkyl group" as the substituent for the "optionally substituted hydrocarbon group" represented by $R^2$. The "protecting group for hydroxy" includes, for example, 2-tetrahydropyranyl, trimethylsilyl, triethylsilyl, tert-butyldiphenylsilyl, and the like.

The "optionally substituted sulfanyl group" as the substituent for the optionally substituted hydrocarbon group" represented by $R^2$ includes, for example, sulfanyl, an alkylsulfanyl group such as methylsulfanyl, ethylsulfanyl, isopropylsulfanyl, tert-butylsulfanyl, etc., an arylsulfanyl group such as phenylsulfanyl, etc., an aralkylsulfanyl group such as benzylsulfanyl, etc. The substituent for the "optionally substituted sulfanyl group" includes a substituent whose type and quantity are the same as those described above for the "optionally substituted lower alkyl group" as the substituent in the "optionally substituted hydrocarbon group" represented by $R^2$.

The "optionally substituted alkylsulfinyl group" as the substituent for the "optionally substituted hydrocarbon group" represented by $R^2$ includes, for example, methylsulfinyl, ethylsulfinyl, isopropylsulfinyl, and the like. The substituent for the "optionally substituted alkylsulfinyl group" includes a substituent whose type and quantity are the same as those described above for the "optionally substituted lower alkyl group" as the substituent in the "optionally substituted hydrocarbon group" represented by $R^2$.

The "optionally substituted arylsulfinyl group" as the substituent for the "optionally substituted hydrocarbon group" represented by $R^2$ includes, for example, benzenesulfinyl, toluenesulfinyl, etc. The substituent for the "optionally substituted arylsulfinyl group" includes a substituent whose type and quantity are the same as those described above for the "optionally substituted lower alkyl group" as the substituent in the "optionally substituted hydrocarbon group" represented by $R^2$.

The "optionally substituted alkylsulfonyl group" as the substituent for the "optionally substituted hydrocarbon group" represented by $R^2$ includes, for example, methylsulfonyl, ethylsulfonyl, isopropylsulfonyl, butylsulfonyl, etc. The substituent for the "optionally substituted alkylsulfonyl group" includes a substituent whose type and quantity are the same as those described above for the "optionally substituted lower alkyl group" as the substituent for the "optionally substituted hydrocarbon group" represented by $R^2$.

The "optionally substituted arylsulfonyl group" as the substituent for the "optionally substituted hydrocarbon group" represented by $R^2$ includes, for example, benzenesulfonyl, toluenesulfonyl, naphthylsulfonyl, etc. The substituent for the "optionally substituted arylsulfonyl group" includes a substituent whose type and quantity are the same as those described above for the "optionally substituted lower alkyl group" as the substituent in the "optionally substituted hydrocarbon group" represented by $R^2$.

The "optionally esterified or amidated sulfonic acid group" as the substituent for the "optionally substituted hydrocarbon group" represented by $R^2$ includes, for example, sulfonic acid group, methyl sulfonate, ethyl sulfonate, sulfonamide, N-methylsulfonamide, etc.

The "optionally substituted amino group" as the substituent for the "optionally substituted hydrocarbon group" represented by $R^2$ includes, for example, an amino, a mono- or di-substituted amino group with an alkyl or an aralkyl group, an acylamino, an alkoxycarbonylamino, an aryloxycarbonylamino, an aralkyloxycarbonylamino, an alkylsulfonylamino or an arylsulfonylamino group, etc.

The "mono- or di-substituted amino group with an alkyl or an aralkyl group" includes, for example, methylamino, ethylamino, isopropylamino, dimethylamino, diethylamino, ethylmethylamino, benzylamino, benzylmethylamino, etc. The "mono- or di-substituted amino group with an alkyl or an aralkyl group" may optionally have a substituent, including a substituent whose type and quantity are the same as those described above for the "optionally substituted lower alkyl group" as the substituent for the "optionally substituted hydrocarbon group" represented by $R^2$.

The "acylamino" includes, for example, foil ylamino, acetylamino, propionylamino, butyrylamino, isobutyrylamino, valerylamino, isovalerylamino, pivaloylamino, benzoylamino, phenacylamino, etc. The "acylamino" may optionally have a substituent, including a substituent whose type and quantity are the same as those described above for the "optionally substituted lower alkyl group" as the substituent for the "optionally substituted hydrocarbon group" represented by $R^2$.

The "alkoxycarbonylamino" includes, for example, methoxycarbonylamino, ethoxycarbonylamino, tert-butoxycarbonylamino, etc. The "alkoxycarbonylamino" may optionally have a substituent, including a substituent whose type and quantity are the same as those described above for the "optionally substituted lower alkyl group" as the substituent in the "optionally substituted hydrocarbon group" represented by $R^2$ described above.

The "aryloxycarbonylamino" includes, for example, phenoxycarbonylamino, naphthyloxycarbonylamino, and the like. The "aryloxycarbonylamino" may optionally have the substituent, including a substituent whose type and quantity are the same as those described above for the "optionally substituted lower alkyl group" as the substituent in the "optionally substituted hydrocarbon group" represented by $R^2$.

The "aralkyloxycarbonylamino" includes, for example, benzyloxycarbonylamino, phenethyloxycarbonylamino, etc. The "aralkyloxycarbonylamino" may optionally have a substituent, including a substituent whose type and quantity are the same as those described above for the "optionally substituted lower alkyl group" as the substituent for the "optionally substituted hydrocarbon group" represented by $R^2$.

The "alkylsulfonylamino" includes, for example, methylsulfonylamino, ethylsulfonylamino, isopropylsulfonylamino, butylsulfonylamino, etc. The "alkylsulfonylamino" may optionally have a substituent, including a substituent whose type and quantity are the same as those described above for the "optionally substituted lower alkyl group" as the substituent in the "optionally substituted hydrocarbon group" represented by $R^2$.

The "arylsulfonylamino" includes, for example, benzenesulfonylamino, naphthylsulfonylamino, etc. The "arylsulfonylamino" may optionally have a substituent, including a substituent whose type and quantity are the same as those described above for the "optionally substituted lower alkyl group" as the substituent in the "optionally substituted hydrocarbon group" represented by $R^2$.

The "optionally substituted heterocyclic group" as the substituent for the "optionally substituted hydrocarbon group" represented by $R^2$ includes, for example, an aliphatic monocyclic nitrogen-containing heterocyclic group, an aromatic monocyclic nitrogen-containing heterocyclic group, a fused nitrogen-containing heterocyclic group, an oxygen-containing monocyclic or fused heterocyclic group, a sulfur-containing monocyclic or fused heterocyclic group, etc.

The "aliphatic monocyclic nitrogen-containing heterocyclic group" includes, for example, aziridinyl, azetidinyl, pyrrolidinyl, imidazolidinyl, pyrazolidinyl, oxazolidinyl, isoxazolidinyl, thiazolidinyl, isothiazolidinyl, piperidyl, piperazyl, pyrazinyl, morpholyl, thiomorpholyl, oxazinyl, thiazinyl, azepinyl, diazepinyl, oxazepinyl, thiazepinyl, etc. The "aliphatic monocyclic nitrogen-containing heterocyclic group" may optionally have a substituent, including a substituent whose type and quantity are the same as those described above for the "optionally substituted lower alkyl group" as the substituent in the "optionally substituted hydrocarbon group" represented by $R^2$.

The "aromatic monocyclic nitrogen-containing heterocyclic group" includes, for example, pyrrolyl, imidazolyl, pyrazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, triazinyl, etc. The "aromatic monocyclic nitrogen-containing heterocyclic group" may optionally have a substituent, including a substituent whose type and quantity are the same as those described above for the "optionally substituted lower alkyl group" as the substituent in the "optionally substituted hydrocarbon group" represented by $R^2$.

The "fused nitrogen-containing heterocyclic group" includes, for example, benzopyrrolidinyl, benzimidazolidinyl, benzopyrazolidinyl, benzoxazolidinyl, benzisoxazolidinyl, benzothiazolidinyl, benzisothiazolidinyl, benzopiperidyl, benzopiperazyl, benzopyrazinyl, benzomorpholyl, benzothiomorpholyl, benzoxazinyl, benzothiazinyl, benzazepinyl, benzodiazepinyl, benzoxazepinyl, benzothiazepinyl, indolyl, isoindolyl, 1H-indazolyl, benzimidazolyl, benzoxazolyl, benzisoxazolyl, benzothiazolyl, benzisothiazolyl, 1H-benzotriazolyl, benzoxadiazolyl, benzothiadiazolyl, quinolyl, isoquinolyl, quinazolinyl, quinoxalinyl, naphthylidinyl, purinyl, puteridinyl, carbazolyl, carbolinyl, acridinyl, phenoxazinyl, phenothiazinyl, phenazinyl, indolidinyl, pyrrolopyridazinyl, pyrrolopyrimidinyl, pyrrolopyrazinyl, pyrrolopyridyl, imidazopyridazinyl, imidazopyrimidinyl, imidazopyrazinyl, imidazopyridyl, thienopyridazinyl, thienopyrimidinyl, thienopyrazinyl, thienopyridyl, thiazolopyridazinyl, thiazolopyrimidinyl, thiazolopyrazinyl, thiazolopyridyl, pyridazopyridazinyl, pyridazopyrimidinyl, pyridazopyrazinyl, pyridazopyridyl, triazolopyridyl, etc. The "fused nitrogen-containing heterocyclic group" may optionally have a substituent, including a substituent whose type and quantity are the same as those described above for the "optionally substituted lower alkyl group" as the substituent in the "optionally substituted hydrocarbon group" represented by $R^2$.

The "oxygen-containing monocyclic or fused heterocyclic group" includes, for example, oxylanyl, oxetanyl, oxolanyl, dioxolanyl, furyl, pyranyl, tetrahydropyranyl, dioxanyl, benzofuranyl, isobenzofuranyl, benzopyranyl, isobenzopyranyl, benzodioxanyl, 7-oxabicyclo[2.2.1]heptyl), 9-oxabicyclo[3.3.1]nonyl, etc. The "oxygen-containing monocyclic or fused heterocyclic group" may optionally have a substituent, including a substituent whose type and quantity are the same as those described above for the "optionally substituted lower alkyl group" as the substituent in the "optionally substituted hydrocarbon group" represented by $R^2$.

The "sulfur-containing monocyclic or fused heterocyclic group" includes, for example, thienyl, thioxolanyl, tetrahydrothiopyranyl, dithianyl, benzothienyl, etc. The "sulfur-containing monocyclic or fused heterocyclic group" may optionally have a substituent, including a substituent whose type and quantity are the same as those described above for the "optionally substituted lower alkyl group" as the substituent in the "optionally substituted hydrocarbon group" represented by $R^2$.

The "alkylenedioxy group" as the substituent for the "optionally substituted hydrocarbon group" represented by $R^2$ includes, for example, methylenedioxy, ethylenedioxy, and the like.

The "optionally substituted cycloalkenyl group" as the substituent for the "optionally substituted hydrocarbon group" represented by $R^2$ includes, for example, a $C_{3-8}$ cycloalkenyl group (e.g., 2-cyclopropenyl, 2-cyclobutenyl, 2-cyclopentenyl, 2-cyclohexenyl, 3-cyclohexenyl, 2-cycloheptenyl, 3-cycloheptenyl, 2-cyclooctenyl, 4-cyclooctenyl, etc.). The substituent which the "cycloalkenyl group" may optionally have includes a substituent whose type and quantity are the same as those described above for the "optionally substituted lower alkyl group" as the substituent in the "optionally substituted hydrocarbon group" represented by $R^2$.

The "optionally substituted heterocyclic group" represented by $R^2$ includes the same "optionally substituted heterocyclic group" as the substituent described above in the "optionally substituted hydrocarbon group" represented by $R^2$.

The hydrocarbon group as the "optionally substituted hydrocarbon group" represented by $R^3$ and $R^4$ includes the same hydrocarbon groups as those described above in the "optionally substituted hydrocarbon group" represented by $R^2$. Preferred hydrocarbon group is a $C_{1-6}$ alkyl group, a $C_{6-10}$ aryl group, a $C_{7-10}$ aralkyl group, or the like.

The substituent for the "optionally substituted hydrocarbon group" represented by $R^3$ and $R^4$ includes a substituent whose type and quantity are the same as those described above for the "optionally substituted hydrocarbon group" represented by $R^2$.

The substituent for the "optionally substituted heterocyclic group" represented by $R^3$ and $R^4$ includes the same "optionally substituted heterocyclic group" as that described above for the "optionally substituted hydrocarbon group" represented by $R^2$.

The nitrogen-containing heterocyclic group in the "optionally substituted nitrogen-containing heterocyclic group formed by $R^3$ and $R^4$ taken together with the nitrogen atom bonded thereto" includes, for example, a monocyclic heterocyclic group having a 3- to 8-membered ring which may optionally contain 1 to 4 hetero atoms selected from oxygen atom, sulfur atom, nitrogen atom, etc., other than carbon atoms, and a bicyclic or tricyclic fused heterocyclic group formed by fusion of a cyclic structure to the 3- to 8-membered ring, and the like. Among others, a nitrogen-containing 5- to 7-membered heterocyclic ring is preferred. Examples of the particularly preferred nitrogen-containing heterocyclic groups include azepinyl, piperidyl, piperazyl, N-methylpiperazyl, pyrrolidyl, morpholyl, and the like.

The substituent for the "optionally substituted nitrogen-containing heterocyclic group fowled by $R^3$ and $R^4$ taken together with the nitrogen atom bonded thereto" includes a substituent whose type and quantity are the same as those described above for the "optionally substituted hydrocarbon group" represented by $R^2$.

Preferably, $R^1$ is —$SR^2$ (wherein $R^2$ represents hydrogen atom, an optionally substituted hydrocarbon group or an optionally substituted heterocyclic group), and more preferably, $R^2$ is an optionally substituted hydrocarbon group. In —$SR^2$, $R^2$ is more preferably an optionally substituted alkyl group (an optionally substituted $C_{1-8}$ alkyl group), an optionally substituted alkenyl group (an optionally substituted $C_{2-8}$ alkenyl group), an optionally substituted aralkyl group (an optionally substituted $C_{7-10}$ aralkyl group) or an optionally substituted cycloalkyl group (an optionally substituted $C_{3-8}$ cycloalkyl group). In —$SR^2$, $R^2$ is even more preferably an optionally substituted $C_{1-8}$ alkyl group, and most preferably, a $C_{4-8}$ alkyl group which may optionally be substituted with a halogen atom.

The hydrocarbon group in the "optionally substituted hydrocarbon group" represented by $R^5$ includes the same hydrocarbon groups as those described above for the "optionally substituted hydrocarbon group" represented by $R^2$. Among others, the hydrocarbon group preferably includes a $C_{1-12}$ alkyl group, a $C_{2-12}$ alkenyl group, a $C_{2-12}$ alkynyl group, a $C_{6-10}$ aryl group, a $C_{7-10}$ aralkyl group, a $C_{3-8}$ cycloalkyl group, a $C_{3-8}$ cycloalkenyl group, etc. Particularly preferred are a $C_{1-8}$ alkyl group, a $C_{2-8}$ alkenyl group, a $C_{6-10}$ aryl group, a $C_{7-10}$ aralkyl group, a $C_{3-8}$ cycloalkyl group and a $C_{3-8}$ cycloalkenyl group. More preferred is a $C_{1-6}$ alkyl group and preferred examples include methyl, ethyl, propyl, isopropyl, butyl, isobutyl, sec-butyl, tert-butyl, pentyl, isopentyl, 2-methylbutyl, hexyl, isohexyl, 2-ethylbutyl, 1,1-dimethylbutyl, 2,2-dimethylbutyl, 3,3-dimethylbutyl, 2,2-dimethylpentyl and 3,3-dimethylpentyl.

The substituent for the "optionally substituted hydrocarbon group" represented by $R^5$ includes a substituent whose type and quantity are the same as those described above for the "optionally substituted hydrocarbon group" represented by $R^2$.

The "acyl group" represented by $R^5$ includes the same "acyl group" as the substituent described above for the "optionally substituted hydrocarbon group" represented by $R^2$.

The "optionally esterified or amidated carboxyl group" represented by $R^5$ includes the same "optionally esterified or amidated carboxyl group" as the substituent described above for the "optionally substituted hydrocarbon group" represented by $R^2$. Among others, preferred are a $C_{2-18}$ alkoxycarbonyl group such as methoxycarbonyl, ethoxycarbonyl, propoxycarbonyl, tert-butoxycarbonyl, hexyloxycarbonyl, dodecyloxycarbonyl, hexadecyloxycarbonyl, etc.

The "optionally substituted heterocyclic group" represented by $R^5$ includes the same "optionally substituted heterocyclic group" as that represented by $R^2$ described above.

The hydrocarbon group in the "optionally substituted hydrocarbon group" represented by $R^6$ includes the same hydrocarbon groups as those described above for the "optionally substituted hydrocarbon group" represented by $R^2$. Preferably, the hydrocarbon group includes a $C_{1-8}$ alkyl group, a $C_{2-8}$ alkenyl group, a $C_{6-10}$ aryl group, a $C_{7-10}$ aralkyl group, etc. Among others, preferred are a $C_{1-6}$ alkyl group, phenyl and benzyl.

The substituent for the "optionally substituted hydrocarbon group" represented by $R^6$ includes a substituent whose type and quantity are the same as those described above for the "optionally substituted hydrocarbon group" represented by $R^2$.

The "acyl group" represented by $R^6$ includes the same "acyl group" as the substituent described above for the "optionally substituted hydrocarbon group" represented by $R^2$.

The "optionally esterified or amidated carboxyl group" represented by $R^6$ includes the same "optionally esterified or amidated carboxyl group" as the substituent described above for the "optionally substituted hydrocarbon group" represented by $R^2$.

The "optionally substituted heterocyclic group" represented by $R^6$ includes the same "optionally substituted heterocyclic group" as the substituent described above for the "optionally substituted hydrocarbon group" represented by $R^2$.

The cyclic hydrocarbon or heterocyclic ring formed by $R^5$ and $R^6$ taken together includes a saturated or unsaturated 5- to 8-membered monocyclic carbon ring or heterocyclic ring, which may optionally contain 1 to 3 atoms selected from nitrogen atom, oxygen atom, sulfur atom, etc., other than carbon atoms, or a bicyclic fused carbon ring or heterocyclic ring containing the above carbon or heterocyclic ring, etc. Examples include a cycloalkyl (e.g., cyclopentyl, cyclohexyl, cycloheptyl, etc.), a cycloalkenyl (e.g., cyclopentenyl, cyclohexenyl, cyclohexadienyl, cycloheptenyl, etc.), an aromatic hydrocarbon ring (e.g., phenyl, naphthyl, etc.), an oxygen-containing ring (e.g., furyl, oxolanyl, tetrahydropyranyl, oxepinyl, benzofuranyl, benzopyranyl, etc.), a nitrogen-containing ring (e.g., pyrrolidyl, piperidyl, pyridyl, azepinyl, indolyl, quinolinyl, benzoazepinyl, etc.), a sulfur-containing ring (e.g., thienyl, tetrahydrothiopyranyl, benzothienyl, etc.) and the like. Among others, particularly preferred are cyclohexyl, cyclopentenyl, cyclohexenyl, phenyl, etc. The cyclic hydrocarbon or heterocyclic ring formed by $R^5$ and $R^6$ taken together may optionally have a substituent, including a substituent whose type and quantity are the same as those described above for the "optionally substituted hydrocarbon group" represented by $R^2$.

Preferably, $R^5$ is an optionally substituted hydrocarbon group, cyano group, acyl group, an optionally esterified or amidated carboxyl group, or an optionally substituted heterocyclic group, and more preferably an optionally substituted hydrocarbon group. Inter alia, preferred are a $C_{1-12}$ alkyl group, a $C_{2-12}$ alkenyl group, a $C_{2-12}$ alkynyl group, a $C_{6-10}$ aryl group, a $C_{7-10}$ aralkyl group, a $C_{3-8}$ cycloalkyl group, a $C_{3-8}$ cycloalkenyl group, etc. In particular, a $C_{1-8}$ alkyl group, a $C_{2-8}$ alkenyl group, a $C_{6-10}$ aryl group, a $C_{7-10}$ aralkyl group, a $C_{3-8}$ cycloalkyl group and a $C_{3-8}$ cycloalkenyl group are more preferred, especially, a $C_{1-6}$ hydrocarbon group, and most preferably a $C_{1-6}$ alkyl group. Specific examples of the preferred $R^5$ include methyl, ethyl, propyl, isopropyl, butyl, isobutyl, sec-butyl, tert-butyl, pentyl, isopentyl, 2-methylbutyl, hexyl, isohexyl, 2-ethylbutyl, 1,1-dimethylbutyl, 2,2-dimethylbutyl and 3,3-dimethylbutyl.

Preferably, $R^6$ is an optionally substituted hydrocarbon group. Among others, a $C_{1-8}$ alkyl group, a $C_{2-8}$ alkenyl group, a $C_{6-10}$ aryl group, a $C_{7-10}$ aralkyl group, etc. are preferred. More preferably, a $C_{1-6}$ hydrocarbon group, with particular preference of a $C_{1-6}$ alkyl group (methyl, ethyl, propyl, isopropyl, butyl, isobutyl, sec-butyl, tert-butyl, pentyl, isopentyl, 2-methylbutyl, hexyl, isohexyl, 2-ethylbutyl, 1,1-dimethylbutyl, 2,2-dimethylbutyl, 3,3-dimethylbutyl, etc., especially methyl and ethyl), and the like.

Furthermore, the compounds where $R^5$ and $R^6$ are taken together to form an optionally substituted benzene ring or an optionally substituted cyclohexane ring are also preferred.

The substituent for the "optionally substituted hydroxy group" represented by $R^7$ includes, for example, an optionally substituted hydrocarbon group, an optionally substituted alkylsulfonyl group, an optionally substituted arylsulfonyl group, an optionally substituted alkylcarbonyl group, an optionally substituted arylcarbonyl group, etc. In the "optionally substituted hydroxy group" represented by $R^7$, hydroxy is preferred.

The "hydrocarbon group" in the optionally substituted hydrocarbon group as the substituent for the "optionally substituted hydroxy group" represented by $R^7$ includes a $C_{1-8}$ alkyl group, a $C_{2-8}$ alkenyl group, a $C_{6-10}$ aryl group, a $C_{7-10}$ aralkyl group, etc. Inter alia, a $C_{1-6}$ alkyl group, benzyl and the like are preferred. The substituent for the optionally substituted hydrocarbon group as the substituent for the "optionally substituted hydroxy group" includes a substituent whose type and quantity are the same as those described above for the "optionally substituted hydrocarbon group" represented by $R^2$.

Examples of the optionally substituted alkylsulfonyl group and optionally substituted arylsulfonyl group as the substituents for the "optionally substituted hydroxy group" represented by $R^7$ include an optionally substituted $C_{1-4}$ alkylsulfonyl group, an optionally substituted benzenesulfonyl group, etc. Among others, methanesulfonyl, trifluoromethanesulfonyl, benzenesulfonyl and toluenesulfonyl are preferred.

Examples of the optionally substituted alkylcarbonyl group and optionally substituted arylcarbonyl group as the substituents for the "optionally substituted hydroxy group" represented by $R^7$ include an optionally substituted $C_{1-4}$ alkylcarbonyl group, an optionally substituted benzoyl group, etc. Among others, acetyl, propionyl and benzoyl are preferred.

The substituent for the optionally substituted alkylsulfonyl group, optionally substituted arylsulfonyl group, optionally substituted alkylcarbonyl group and optionally substituted arylcarbonyl group as the substituent for the "optionally substituted hydroxy group" represented by $R^7$ includes a substituent whose type and quantity are the same as those described above for the "optionally substituted hydrocarbon group" represented by $R^2$.

The hydrocarbon group in the "optionally substituted hydrocarbon group" represented by $R^8$ and $R^9$ includes the same hydrocarbon group as that described above in the "optionally substituted hydrocarbon group" represented by $R^2$, preferably a $C_{1-8}$ alkyl group, a $C_{2-8}$ alkenyl group, a $C_{6-10}$ aryl group, a $C_{7-10}$ aralkyl group, etc. Among others, a $C_{1-6}$ alkyl group, phenyl and benzyl are preferred.

The substituent for the "optionally substituted hydrocarbon group" represented by $R^8$ and $R^9$ includes a substituent whose type and quantity are the same as those described above for the "optionally substituted hydrocarbon group" represented by $R^2$.

The cyclic hydrocarbon or heterocyclic ring formed by $R^5$ and $R^8$ taken together includes a saturated or unsaturated 5- to 8-membered monocyclic carbon ring or heterocyclic ring, which may optionally contain 1 to 3 atoms selected from nitrogen atom, oxygen atom, sulfur atom, etc., other than carbon atoms, or a bicyclic fused carbon ring or heterocyclic ring containing the above carbon or heterocyclic ring, etc. Examples include a cycloalkyl (e.g., cyclopentyl, cyclohexyl, cycloheptyl, etc.), a cycloalkenyl (e.g., cyclopentenyl, cyclohexenyl, cyclohexadienyl, cycloheptenyl, etc.), an aromatic hydrocarbon ring (e.g., phenyl, naphthyl, etc.), an oxygen-containing ring (e.g., furyl, oxolanyl, tetrahydropyranyl, oxepinyl, benzofuranyl, benzopyranyl, etc.), a nitrogen-containing ring (e.g., pyrrolidyl, piperidyl, pyridyl, azepinyl, indolyl, quinolinyl, benzoazepinyl, etc.); a sulfur-containing ring (e.g., thienyl, tetrahydrothiopyranyl, benzothienyl, etc.) and the like. Among others, particularly preferred are cyclohexenyl, phenyl, etc. The cyclic hydrocarbon or heterocyclic ring formed by $R^5$ and $R^8$ taken together may optionally have a substituent, including a substituent whose type and quantity are the same as those described above for the "optionally substituted hydrocarbon group" represented by $R^2$. The cyclic hydrocarbon or heterocyclic ring formed by $R^8$ and $R^9$ taken together includes a saturated or unsaturated 5- to 8-membered monocyclic carbon ring or heterocyclic ring, which may optionally contain 1 to 3 atoms selected from nitrogen atom, oxygen atom, sulfur atom, etc., other than carbon atoms, or a bicyclic fused carbon ring or heterocyclic ring containing the above carbon or heterocyclic ring, etc. Examples include a cycloalkyl (e.g., cyclopentyl, cyclohexyl, cycloheptyl, etc.), a cycloalkenyl (e.g., cyclopentenyl, cyclohexenyl, cyclohexadienyl, cycloheptenyl, etc.), an aromatic hydrocarbon ring (e.g., phenyl, naphthyl, etc.), an oxygen-containing ring (e.g., furyl, oxolanyl, tetrahydropyranyl, oxepinyl, benzofuranyl, benzopyranyl, etc.), a nitrogen-containing ring (e.g., pyrrolidyl, piperidyl, pyridyl, azepinyl, indolyl, quinolinyl, benzoazepinyl, etc.), a sulfur-containing ring (e.g., thienyl, tetrahydrothiopyranyl, benzothienyl, etc.) and the like. The cyclic hydrocarbon or heterocyclic ring formed by $R^8$ and $R^9$ taken together may optionally have a substituent, including a substituent whose type and quantity are the same as those described above for the "optionally substituted hydrocarbon group" represented by $R^2$.

An optionally substituted hydrocarbon group is preferred as $R^8$ and $R^9$, more preferably, a $C_{1-8}$ alkyl group, a $C_{2-8}$ alkenyl group, a $C_{6-10}$ aryl group and a $C_{7-10}$ aralkyl group, and most preferably, a $C_{1-6}$ alkyl group, phenyl and benzyl.

$R^{10}$ represents hydrogen atom, —$ZR^{15}$ or —$P(O)R^{16}R^{17}$.

The hydrocarbon group in the "optionally substituted hydrocarbon group" represented by $R^{15}$ in –$ZR^{15}$ includes the same hydrocarbon group as that described above in the "optionally substituted hydrocarbon group" represented by $R^2$. Preferably, the hydrocarbon group includes a $C_{1-12}$ alkyl group, a $C_{2-12}$ alkenyl group, a $C_{2-12}$ alkynyl group, a $C_{6-10}$ aryl group, a $C_{7-10}$ aralkyl group, a $C_{3-8}$ cycloalkyl group, a $C_{3-8}$ cycloalkenyl group, etc. Among others, a $C_{6-10}$ aryl group, a $C_{7-10}$ aralkyl group, a $C_{3-8}$ cycloalkyl group and the like are more preferred.

The substituent for the "optionally substituted hydrocarbon group" represented by $R^{15}$ includes a substituent whose type and quantity are the same as those described above for the "optionally substituted hydrocarbon group" represented by $R^2$. Among others, the substituents include an optionally substituted $C_{1-4}$ alkyl group, an optionally substituted $C_{2-4}$ alkenyl group, a halogen atom such as fluorine, chlorine, bromine, etc., a $C_{1-4}$ alkoxy group, a $C_{1-4}$ haloalkyl group, carboxyl, carboxamido, etc. Examples of the particularly preferred substituents are methyl, ethyl, propyl, isopropyl, vinyl, fluorine, chlorine, bromine, methoxy, ethoxy, and the like.

The "optionally substituted heterocyclic group" represented by $R^{15}$ in –$ZR^{15}$ includes the same "optionally substituted heterocyclic group" as the substituent described above for the "optionally substituted hydrocarbon group" represented by $R^2$. Among others, examples of the preferred heterocyclic group include an optionally substituted thienyl group, an optionally substituted quinolyl group, an optionally substituted benzoxadiazolidinyl group, an optionally substituted pyridyl group, an optionally substituted benzothiadiazolyl group, an optionally substituted benzothienyl group, an optionally substituted oxazolidinyl group, an optionally substituted benzodioxanyl group, an optionally substituted dibenzofuranyl group and morpholyl, and more preferably, an optionally substituted thienyl group, an optionally substituted benzothiadiazolyl group and an optionally substituted pyridyl group.

Z represents —$SO_2$—, —$SO$—, —$CONR^{18}SO_2$— (wherein $R^{18}$ is a $C_{1-6}$ alkyl), —$CONR^{19}$— (wherein $R^{19}$ is a $C_{1-6}$ alkyl) or —$CO$—. The $C_{1-6}$ alkyl represented by $R^{18}$ and $R^{19}$ includes, for example, methyl, ethyl, propyl, isopropyl, butyl, isobutyl, sec-butyl, tert-butyl, pentyl, hexyl, etc.

The "optionally substituted hydrocarbon group" represented by $R^{16}$ and $R^{17}$ includes the same hydrocarbon group as the "optionally substituted hydrocarbon group" represented by $R^2$ described above. Preferably, the hydrocarbon group is a $C_{1-12}$ alkyl group, a $C_{2-12}$ alkenyl group, a $C_{2-12}$ alkynyl group, a $C_{6-10}$ aryl group, a $C_{7-10}$ aralkyl group, a $C_{3-8}$ cycloalkyl group, a $C_{3-8}$ cycloalkenyl group, etc. Among others, a $C_{1-6}$ alkyl group, a $C_{6-10}$ aryl group, a $C_{7-10}$ aralkyl group, etc. are preferred, more preferably, methyl, ethyl, phenyl, benzyl, etc.

The substituent for the "optionally substituted hydrocarbon group" represented by $R^{16}$ and $R^{17}$ includes a substituent whose type and quantity are the same as those described above for the "optionally substituted hydrocarbon group" represented by $R^2$.

The "optionally substituted hydroxy group" represented by $R^{16}$ and $R^{17}$ includes, for example, an optionally substituted hydrocarbon group.

The "hydrocarbon group" in the optionally substituted hydrocarbon group as the substituent for the "optionally substituted hydroxy group" represented by $R^{16}$ and $R^{17}$ includes a $C_{1-8}$ alkyl group, a $C_{2-8}$ alkenyl group, a $C_{6-10}$ aryl group, a $C_{7-10}$ aralkyl group, etc. Among others, a $C_{1-6}$ alkyl group, a $C_{6-10}$ aryl group, a $C_{7-10}$ aralkyl group, etc. are preferred, and more preferably, methyl, ethyl, propyl, butyl, phenyl, benzyl, etc. The substituent for the optionally substituted hydrocarbon group as the substituent for the "optionally substituted hydroxy group" includes a substituent whose type and quantity are the same as those described above for the "optionally substituted hydrocarbon group" represented by $R^2$.

The "optionally substituted hydroxy group" represented by $R^{16}$ and $R^{17}$ is preferably a hydroxy group substituted with a $C_{1-6}$ alkyl group, a $C_{6-10}$ aryl group, etc.

The "optionally substituted amino group" represented by $R^{16}$ and $R^{17}$ includes the same "optionally substituted amino group" as the substituent described above for the "optionally substituted hydrocarbon group" represented by $R^2$, and preferably, methyl, ethyl, phenyl, benzyl, etc.

Preferably, $R^{16}$ and $R^{17}$ include a $C_{1-6}$ alkyl group, a $C_{6-10}$ aryl group, a hydroxy group substituted with a $C_{1-6}$ alkyl group, a hydroxy group substituted with a $C_{6-10}$ aryl group, etc., and more preferably, methyl, ethyl, phenyl, benzyl, hydroxy substituted with methyl, hydroxy substituted with ethyl, hydroxy substituted with phenyl, etc.

Preferably, $R^{10}$ is —$ZR^{15}$ (wherein Z and $R^{15}$ have the same significance as defined above). Preferred is the case where Z is —$SO_2$— or —$CO$— and $R^{15}$ is an optionally substituted aryl group, an optionally substituted aralkyl group or an optionally substituted heterocyclic group. More preferred is the case where Z is —$SO_2$— or —$CO$— and $R^{15}$ is an optionally substituted $C_{6-10}$ aryl group, an optionally substituted $C_{7-10}$ aralkyl group or an optionally substituted heterocyclic group. Even more preferred is the case where Z is —$SO_2$— and $R^{15}$ is a phenyl, benzyl, thienyl or benzothiadiazolyl group substituted with methyl, ethyl, propyl, isopropyl, vinyl, fluorine, chlorine, bromine, methoxy, ethoxy, etc., or where Z is —$CO$— and $R^{15}$ is a pyridyl group substituted with methyl, ethyl, propyl, isopropyl, vinyl, fluorine, chlorine, bromine, methoxy, ethoxy, etc.

$R^{11}$ represents hydrogen atom or an optionally substituted hydrocarbon group. The hydrocarbon group in the "optionally substituted hydrocarbon group" represented by $R^{11}$ described above includes the same hydrocarbon group as that described in the "optionally substituted hydrocarbon group" represented by $R^2$. Preferably, the hydrocarbon group is a $C_{1-6}$ alkyl group, a $C_{2-6}$ alkenyl group, a $C_{7-10}$ aralkyl group, etc. Among others, a $C_{1-6}$ alkyl group and benzyl are preferred, and more preferably, a $C_{1-4}$ alkyl group, etc. The substituent for the "optionally substituted hydrocarbon group" represented by $R^{11}$ includes a substituent whose type and quantity are the same as those described above for the "optionally substituted hydrocarbon group" represented by $R^2$.

$R^{11}$ is preferably hydrogen atom.

The nitrogen-containing heterocyclic ring which may be formed by $R^{10}$ and $R^{11}$ taken together refers to a 5- to 8-membered nitrogen-containing heterocyclic ring wherein a partial structure represented by the following formula:

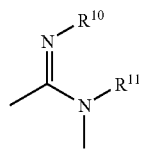

is represented by:

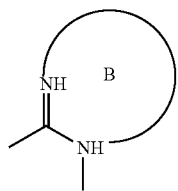

(wherein the ring B is an optionally substituted 5- to 8-membered). More specifically, the heterocyclic ring refers to a ring represented by the following formula:

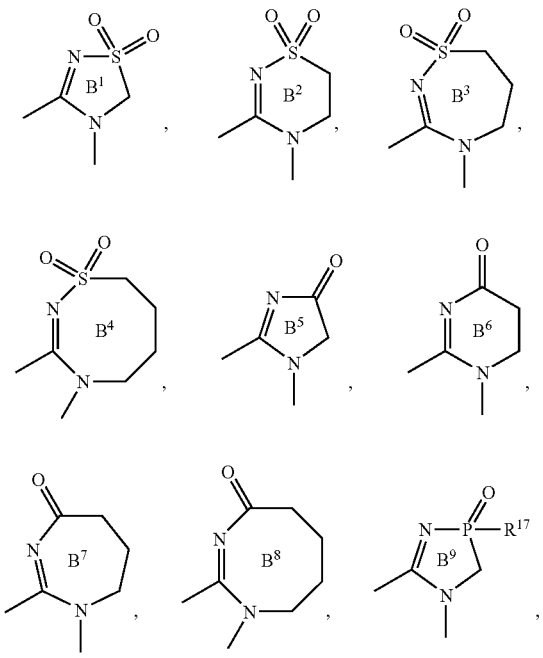

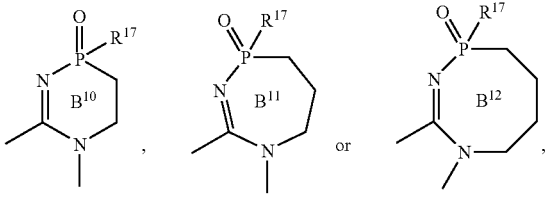

wherein $R^{17}$ has the same significance as defined above and the rings $B^1$ to $B^{12}$ represent nitro-containing heterocyclic rings each of which may have additional substituent. The substituent which the rings $B^1$ to $B^{12}$ may have represents the same substituents the "optionally substituted hydrocarbon group" represented by R'5 described above may have.

The nitrogen-containing heterocyclic ring which may be formed by $R^{10}$ and $R^{11}$ taken together is preferably a 6- or 7-membered nitrogen-containing heterocyclic ring wherein a structure represented by the following formula:

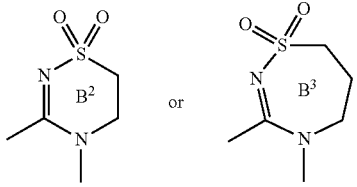

(wherein the ring $B^2$ or $B^3$ represents a nitrogen-containing heterocyclic group which may further be substituted).

The hydrocarbon group in the "optionally substituted hydrocarbon group" represented by $R^{12}$ and $R^{13}$ includes the same hydrocarbon group as that described above in the "optionally substituted hydrocarbon group" represented by $R^2$. The hydrocarbon group is preferably a $C_{1-12}$ alkyl group, a $C_{2-12}$ alkenyl group, a $C_{2-12}$ alkynyl group, a $C_{6-10}$ aryl group, a $C_{7-10}$ aralkyl group, a $C_{3-8}$ cycloalkyl group, a $C_{3-8}$ cycloalkenyl group, etc. Among others, a $C_{1-12}$ alkyl group, a $C_{2-12}$ alkenyl group and a $C_{7-10}$ aralkyl group are preferred. The substituent for the "optionally substituted hydrocarbon group" represented by $R^{12}$ and $R^{13}$ includes a substituent whose type and quantity are the same as those described above for the "optionally substituted hydrocarbon group" represented by $R^2$.

Examples of the optionally substituted nitrogen-containing heterocyclic group formed by $R^{12}$ and $R^{13}$ taken together with the nitrogen atom bonded thereto include the same heterocyclic group as the "optionally substituted nitrogen-containing heterocyclic group formed by $R^3$ and $R^4$ taken together with the nitrogen atom bonded thereto" described above. Particularly preferred examples include piperidyl, piperazyl, N-methylpiperazyl, pyrrolidyl, morpholyl, and the like.

The substituent for the "optionally substituted nitrogen-containing heterocyclic group formed by $R^{12}$ and $R^{13}$ taken together with the nitrogen atom bonded thereto" includes a substituent whose type and quantity are the same as those described above for the "optionally substituted hydrocarbon group" represented by $R^2$.

Preferably, $R^{12}$ is hydrogen atom, a $C_{1-12}$ alkyl group, a $C_{2-12}$ alkenyl group, a $C_{2-12}$ alkynyl group, a $C_{6-10}$ aryl group, a $C_{7-10}$ aralkyl group, a $C_{3-8}$ cycloalkyl group, a $C_{3-8}$ cycloalkenyl group, etc. Among others, a $C_{1-12}$ alkyl group, a $C_{2-12}$ alkenyl group and a $C_{7-10}$ aralkyl group are particularly preferred.

Preferably, $R^{13}$ is hydrogen atom.

The hydrocarbon group in the "optionally substituted hydrocarbon group" represented by $R^{14}$ includes the same hydrocarbon group as that described above in the "optionally substituted hydrocarbon group" represented by $R^2$. Preferably, the hydrocarbon group includes a $C_{1-12}$ alkyl group, a $C_{2-12}$ alkenyl group, a $C_{2-12}$ alkynyl group, a $C_{6-10}$ aryl group, a $C_{7-10}$ aralkyl group, a $C_{3-8}$ cycloalkyl group, a $C_{3-8}$ cycloalkenyl group, etc. Among others, a $C_{1-4}$ alkyl group and a $C_{7-10}$ aralkyl group are preferred. The substituent for the "optionally substituted hydrocarbon group" represented by $R^{14}$ includes a substituent whose type and quantity are the same as those described above for the "optionally substituted hydrocarbon group" represented by $R^2$. Examples of $-ZR^{15}$ represented by $R^{14}$ are the same as those in $-ZR^{15}$ represented by $R^{10}$.

Preferably, $R^{14}$ is an optionally substituted hydrocarbon group. Among others, a $C_{1-12}$ alkyl group, a $C_{2-12}$ alkenyl group, a $C_{2-12}$ alkynyl group, a $C_{7-10}$ aralkyl group, a $C_{3-8}$ cycloalkyl group, a $C_{3-8}$ cycloalkenyl group, etc., and more preferably, a $C_{1-6}$ alkyl group and a $C_{7-10}$ aralkyl group.

Preferably,

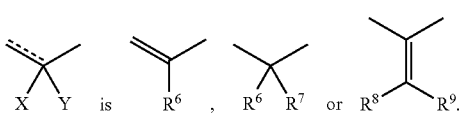

Among others,

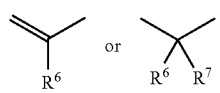

is preferred, and more preferably,

Preferably,

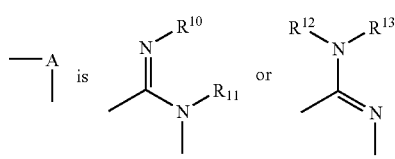

and more preferably,

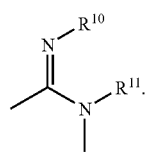

Preferably used as Compound (I) is the compound represented by the formula:

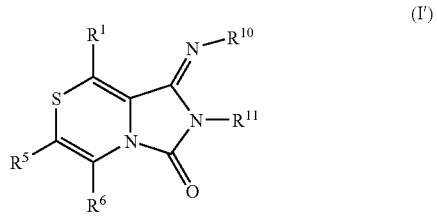

(wherein each symbol has the same significance as defined above). Among others, preferably used is the compound wherein:

$R^1$ is $-SR^2$;

$R^2$ is a $C_{1-8}$ alkyl group, $C_{2-8}$ alkenyl group, $C_{7-10}$ aralkyl group or $C_{3-8}$ cycloalkyl group, which may optionally be substituted (preferably, a $C_{4-8}$ alkyl group which may optionally be substituted with a halogen atom);

$R^5$ is a $C_{1-12}$ alkyl group, $C_{2-12}$ alkenyl group, $C_{2-12}$ alkynyl group, $C_{6-10}$ aryl group, $C_{7-10}$ aralkyl group, $C_{3-8}$ cycloalkyl group or $C_{3-8}$ cycloalkenyl group, which may optionally be substituted (preferably, a $C_{1-12}$ alkyl group);

$R^6$ is a $C_{1-8}$ alkyl group, $C_{2-8}$ alkenyl group, $C_{6-10}$ aryl group or $C_{7-10}$ aralkyl group, which may optionally be substituted (preferably, a $C_{1-6}$ alkyl group);

$R^{10}$ is $-SO_2-R^{15}$;

$R^{15}$ is a $C_{6-10}$ aryl group, $C_{7-10}$ aralkyl group or a 5- to 6-membered heterocyclic group, which may optionally be substituted (preferably, a $C_{1-6}$ aryl group and/or a phenyl, benzyl, thienyl or benzothiadiazolyl group substituted with a halogen atom); and, $R^{11}$ is hydrogen atom.

Preferred salts of Compound (I) described above are pharmacologically acceptable salts and include, for example, salts with inorganic bases, salts with organic bases, salts with inorganic acids, salts with organic acids, salts with basic or acidic amino acids, etc.

Preferred examples of the salts with inorganic bases include alkali metal salts such as sodium salts, potassium salts, etc., alkaline earth metal salts such as calcium salts, magnesium salts, etc., and aluminum salts, ammonium salts, etc.

Preferred examples of the salts with organic bases include salts with, e.g., trimethylamine, triethylamine, pyridine, picoline, ethanolamine, diethanolamine, triethanolamine, dicyclohexylamine, N,N'-dibenzylethylenediamine, etc.

Preferred examples of the salts with inorganic acids include salts with, e.g., hydrochloric acid, hydrobromic acid, nitric acid, sulfuric acid, phosphoric acid, etc.

Preferred examples of the salts with organic acids include salts with, e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

Preferred examples of the salts with basic amino acids include salts with, e.g., arginine, lysine, ornithine, etc. Preferred examples of the salts with acidic amino acids include salts with, e.g., aspartic acid, glutamic acid, etc.

Compound (I) may be hydrated or non-hydrated. Additionally, Compound (I) used in the present invention may have one asymmetric carbon in the skeleton and two optical isomers may be present. Each of these isomers and mixtures thereof is included in the present invention. Furthermore, where their substituents may contain asymmetric carbons or unsaturated bonds, steric isomers or geometric isomers are formed. Each of these isomers and mixtures thereof is included in the present invention as well.

Compound (I) contains sulfur atoms in its structure. These sulfur atoms may be oxidized in a conventional manner using an oxidizing agent (e.g., hydrogen peroxide, m-chloroperbenzoic acid, etc.). These sulfoxides and sulfonated compounds are also included in the present invention. Compound (I) may optionally contain an amido, imido, amidino, guanidino or ureido group in its structure or substituent. These compounds may take resonance structures where the double bonds are isomerized. These compounds with the resonance structures are also included in the present invention.

Compound (I) can be produced by the method described in WO 02/92606 or by its modifications. The imidazothiazine derivative which can be used in the step (1) includes 5-[[(1Z)-5,6-dimethyl-3-oxo-1-([[4-(trifluoromethyl)phenyl]sulfonyl]imino)-2,3-dihydro-1H-imidazo[5,1-c][1,4]thiazin-8-yl]sulfanyl]pentanoic acid wherein a carboxyl group is introduced at the terminus in such a manner that can be bound to a carrier. The compound can be produced by the method described in EXAMPLE 21-10 in WO 02/92606 or by its modifications.

An embodiment of the step (1) which comprises measuring and comparing (i) the binding level of an immobilized imidazothiazine derivative to Hsp90 in the absence of a test compound and (ii) the binding level of an immobilized imidazothiazine derivative to Hsp90 in the presence of the test compound is described below.

First, Hsp90 and a test compound in various concentrations are mixed in an appropriate buffer solution and the mixture is reacted for a given period of time. When the test compound has the binding property to Hsp90, a complex of the test compound and Hsp90 is formed. Next, the immobilized imidazothiazine derivative is added to the mixture, and the resulting mixture is reacted for another given period of time. During this reaction, Hsp90 which does not form the complex with the test compound reacts with the immobilized imidazothiazine derivative. After completion of the reaction, the immobilized imidazothiazine derivative is washed with a buffer solution to remove the Hsp90 unbound to the imidazothiazine derivative. The immobilized imidazothiazine derivative after washing is mixed with a buffer solution and the mixture is heat-treated to elute the Hsp90 bound to the imidazothiazine derivative into the buffer solution. The same procedures as described above are proceeded in the absence of the test compound to obtain the eluate.

Next, the eluate is applied to SDS polyacrylamide gel electrophoresis. After completion of the electrophoresis, the gel is stained and the Hsp90 bound to the imidazothiazine derivative is detected as a band. The bands of Hsp90 (protein levels of Hsp90) obtained in the absence of the test compound and in the presence of the test compound are compared. When the protein level of Hsp90 obtained in the presence of the test compound is lower than that in the absence of the test compound, it can be determined that the test compound has the activity of inhibiting the binding property of Hsp90 to the imidazothiazine derivative, i.e., has the Hsp90 binding activity.

Next, an embodiment of the step (1) which comprises measuring and comparing (i) the binding level of immobilized Hsp90 to a labeled imidazothiazine derivative in the absence of a test compound and (ii) the binding level of immobilized Hsp90 to a labeled imidazothiazine derivative in the presence of the test compound is described below.

First, an imidazothiazine derivative is labeled using tritium as a radioactive isotope to give a labeled imidazothiazine derivative. Immobilized Hsp90 bound to beads containing a scintillator, the labeled imidazothiazine derivative and a test compound in various concentrations are mixed in an appropriate buffer and the mixture is reacted for a given period of time. When the test compound has the binding property to Hsp90, the test compound binds to the immobilized Hsp90. On the other hand, the labeled imidazothiazine derivative binds to the immobilized Hsp90 unbound to the test compound. After completion of the reaction, the radioactivities of the labeled imidazothiazine derivative bound to the immobilized Hsp90 are measured and compared in the absence and presence of a test compound using a scintillator counter. When the radioactivity in the presence of the test compound is lower than that in the absence of the test compound, it can be determined that the test compound has the activity of inhibiting the binding property of Hsp90 to the imidazothiazine derivative, i.e., has the Hsp90 binding activity.

In an embodiment other than the embodiments described above, the step (1) of the invention comprises measuring the binding level of immobilized Hsp90 to a test compound by surface plasmon resonance measurement. Specifically, Hsp90 is immobilized on a sensor chip surface of, e.g., a surface plasmon sensor (manufactured by Biacore, BIACORE 3000, etc.), and a test compound dissolved in an appropriate buffer solution is then passed over the surface of the chip, whereby changes in surface plasmon resonance are monitored to screen a test compound having the Hsp90 binding activity.

According to the step (1), a test compound having the Hsp90 binding activity is screened and the test compound is further subjected to the steps (2) and (3). Thus, an excellent cell protecting agent can be obtained.

For the purpose of screening a test compound having the heat shock protein expression-inducing activity, a test compound is examined in the step (2) for the heat shock protein expression-inducing activity of the test compound.

The heat shock protein expression-inducing activity can be measured in a cell or cell extract system capable of expressing the heat shock protein using as an indicator the heat shock protein or mRNA encoding the heat shock protein. A preferred embodiment of the step (2) includes measuring the heat shock protein expression-inducing activity of a test compound using a cell capable of expressing a heat shock protein. The heat shock protein in the step (2) includes, for example, one or more selected from the group consisting of Hsp40, Hsp70 and Hsp90.

The embodiment of the step (2) which comprises measuring the heat shock protein expression-inducing activity of a test compound using a cell capable of expressing a heat shock protein is described below.

As the cell capable of expressing a heat shock protein, a human normal articular chondrocyte capable of expressing Hsp70 is used. First, the cell is grown in a growth medium for monolayer culture and then inoculated into a multiwell plate followed by further incubation. A test compound and IL-1β are added and incubation is performed for a given period of time. After completion of the incubation, the plate is washed with a buffer solution and a cell lysis buffer is then added thereto. The cell debris is scraped from the plate using a cell scraper and the cell lysis buffer is recovered. The recovered cell lysis buffer is mixed with a sample buffer. After heat-treatment at 95° C. for 5 minutes, the mixture is subjected to SDS polyacrylamide electrophoresis. After completion of the electrophoresis, the protein in the gel is adsorbed onto a nitrocellulose membrane. The protein level of Hsp70 is measured by western blotting using anti-Hsp70 antibody as a primary antibody and horseradish peroxidase-labeled anti-mouse IgG antibody as a secondary antibody.

When a test compound increases the protein level of Hsp70 in human normal articular chondrocytes in the presence of IL-1β stimulation, it can be determined that the test compound has the heat shock protein expression-inducing activity.

By the way, compounds having the activity of disrupting the Hsp90/HSF-1 complex are known to induce the expression of heat shock proteins (Non-Patent Document 1). Accordingly, the heat shock protein expression-inducing activity of a test compound in the step (2) can be determined by assaying the activity of a test compound to disrupt the Hsp90/HSF-1 complex.

HSF-1 refers to a heat shock factor (heat shock factor-1) and is not particularly limited so long as it forms a complex with Hsp90.

HSF-1 which can be used is those derived from various animals, especially from human. As human HSF-1, for example, human HSF-1 (GenBank accession No. NP_005517) can be used. HSF-1 of the present invention also includes salts of the HSF-1 proteins and modified HSF-1 proteins.

An embodiment of the step (2) which comprises measuring the activity of disrupting the Hsp90/HSF-1 complex is described below.

First, human normal articular chondrocytes are lysed in a buffer solution containing a proteinase inhibitor. The lysate is centrifuged and the resulting supernatant is used as the lysate containing the Hsp90/HSF-1 complex. To a dilution of the above lysate in an appropriate buffer solution, a test compound or a buffer solution is added and the mixture is reacted for a given period of time. When the test compound has the activity of disrupting the Hsp90/HSF-1 complex, Hsp90 and HSF-1 are dissociated from the complex. Thereafter, an anti-Hsp90 antibody or a control antibody is added to the reaction solution for immunoprecipitation. When the Hsp90/HSF-1 complex is present in the reaction system, the anti-Hsp90 antibody/Hsp90/HSF-1 complex is formed. When Hsp90 dissociated from HSF-1 is present in the reaction system, the anti-Hsp90 antibody/Hsp90 complex is formed.

Next, protein A/G agarose is added to the system. The mixture is reacted for a given period of time to adsorb the antibody to protein A/G agarose. Subsequently, protein A/G agarose is recovered by centrifugation. After washing with a buffer solution, protein A/G agarose is mixed with a sample buffer, followed by heat treatment for 5 minutes. The protein bound to protein A/G agarose is eluted and the eluate is subjected to SDS polyacrylamide electrophoresis.

After completion of the electrophoresis, the protein in the gel is adsorbed onto a nitrocellulose membrane. The Hsp90 and HSF-1 proteins are detected as bands by western blotting using an anti-HSF-1 antibody or anti-Hsp90 antibody as a primary antibody and a horseradish peroxidase-labeled anti-IgG antibody as a secondary antibody. The bands of the proteins (protein levels) detected in the absence of a test compound or in the presence of the test compound are compared. When the protein level of HSF-1 in the presence of the test compound is lower than that in the absence of the test compound, it can be determined that the test compound has the activity of disrupting the Hsp90/HSF-1 complex, namely, the heat shock protein expression-inducing activity.

According to the step (2), a test compound having the heat shock protein expression-inducing activity is screened and the test compound is further subjected to the steps (1) and (3). Thus, an excellent cell protecting agent can be obtained.

For the purpose of screening a test compound having the activity of inducing the degradation of an Hsp90 client protein, the Hsp90 client protein degradation-inducing activity of a test compound is examined in the step (3).

The Hsp90 client protein degradation-inducing activity can be measured by using a cell or cell extract system capable of expressing a client protein. A preferred embodiment of the step (3) includes, for example, a step which comprises measuring and comparing (i) the level of an Hsp90 client protein in a cell in the absence of a test compound and (ii) the level of an Hsp90 client protein in a cell in the presence of the test compound.

The Hsp90 client protein is not particularly limited as far as it is a protein having a property to form a complex with Hsp90 for its stable presence or normal functions in a cell, and includes, for example, one or more proteins selected from the group consisting of a glucocorticoid receptor, an Akt and a cycline dependent kinase 4. Examples of glucocorticoid receptors include those from various animals, especially from human, e.g., human glucocorticoid receptor (GENBANK Accession No. AAB20466).

The Akt is one of serine/threonine kinases (EC 2.7.11.1). Examples of Akt include those from various animals, especially from human, e.g., human Akt (GENBANK Accession No. NP_001014432).

The cycline dependent kinase 4 is a kinase activated through formation of the complex with cycline D. Examples of the cycline dependent kinase 4 include those from various animals, especially from human, e.g., human cycline dependent kinase 4 (GENBANK Accession No. NP000066). Examples of the Hsp90 client protein are EGF-R (epidermal growth factor receptor), IGFIR (insulin-like growth factor I receptor), RIP (receptor-interacting protein), etc.

The level of an Hsp90 client protein can be measured by, e.g., western blotting using an antibody against the Hsp90 client protein An embodiment of the step (3) which comprises measuring and comparing (i) the level of an Hsp90 client protein in a cell in the absence of a test compound and (ii) the level of an Hsp90 client protein in a cell in the presence of the test compound is described below.

First, human normal articular chondrocytes are suspended in a medium and inoculated in a multiplate, followed by incubation for a given period of time. The culture cells are used as the cells capable of expressing the client protein of Hsp90. Next, a test compound is added to the culture broth and the cells are incubated for another given period of time. After completion of the incubation, the cells are washed once with a buffer solution and a cell lysis buffer is added thereto. After the cell debris is scraped from the plate using a cell scraper, the cell lysis buffer is recovered. The recovered cell lysis buffer is mixed with a sample buffer. The mixture is then heat-treated and subjected to SDS polyacrylamide electrophoresis using Multigel (manufactured by Daiichi Pure Chemicals Co., Ltd.).

After completion of the electrophoresis, the proteins in the gel are adsorbed onto a nitrocellulose membrane. The client proteins are detected as bands by western blotting. When the client proteins are glucocorticoid receptor, Akt and cycline dependent kinase 4, an antibody against each protein is used as a primary antibody and a horseradish peroxidase-labeled anti-IgG antibody as a secondary antibody.

The bands of proteins (protein levels) detected in the absence of the test compound and in the presence of the test compound are compared. When there is no substantial difference in the protein levels of the client protein in the absence of the test compound and in the presence of the test compound, it can be determined that the test compound shows no client protein degradation-inducing activity. On the other hand, when the protein level of the client protein in the presence of the test compound is lower than that in the absence of the test compound, it can be determined that the test compound has the Hsp90 client protein degradation-inducing activity.

According to the step (3), a test compound having no Hsp90 client protein degradation-inducing activity is screened and the test compound is further subjected to the steps (1) and (2). Thus, an excellent cell protecting agent can be obtained.

According to the present invention, the order of these steps performed is not particularly limited. Two or three steps may be performed concurrently. Furthermore, the steps (2) and (3) are preferably performed using a cell capable of expressing a protein. Specifically, it is preferred that the step (2) is measuring the heat shock protein expression-inducing activity of a test compound using a cell capable of expressing a heat shock protein, and the step (3) is measuring the Hsp90 client protein degradation-inducing activity of a test compound using a cell capable of expressing a Hsp90 client protein.

The method for screening the cell protecting agent of the invention may be a method which comprises applying the following steps (1) to (4) to a test compound: (1) measuring the binding property of a test compound to Hsp90, (2) measuring the activity of a test compound to induce the expression of a heat shock protein, (3) measuring the activity of a test compound to induce the degradation of an Hsp90 client protein, and (4) screening a test compound which shows the Hsp90 binding activity and the heat shock protein expression-inducing activity but does not show the Hsp90 client protein degradation-promoting activity.

The objects and embodiments of the steps (1) to (3) are the same as described above. The order of each step performed is not particularly limited. In the steps (1) to (3), two or three steps may be performed concurrently. The step (4) is screening a test compound which shows the Hsp90 binding activity and the heat shock protein expression-inducing activity but does not show the Hsp90 client protein degradation-promoting activity, based on the measurement results in the steps (1) to (3).

According to the screening method of the present invention, an excellent cell protecting agent showing a minimized cytotoxicity or no cytotoxicity, that is, "the cell protecting agent showing the Hsp90 binding activity and the heat shock protein expression-inducing activity with a minimized activity of promoting the degradation of an Hsp90 client protein or without any such activity" or "the cell protecting agent showing the Hsp90 binding activity and the activity of disrupting the Hsp90/HSF-1 complex as well as having minimized or no activity of promoting the degradation of an Hsp90 client protein" can be obtained. The cell protecting agent is useful as an agent for the prevention/treatment of, for example, heart diseases (e.g., myocardiopathy, heart failure, angina pectoris, myocardial infarction, etc.), neurological disorders (e.g., Parkinson's disease, Alzheimer's disease, triplet repeat disease, prion disease, amyotrophic lateral sclerosis cerebellar degeneration, retinitis pigmentosa, etc.), brain diseases (e.g., cerebral infarction, etc.), central neuron infectious diseases (e.g., HIV encephalitis, bacterial meningitis, etc.), traumatic injuries (e.g., spinal cord injury, brain damage, etc.), demyelinating diseases (e.g., multiple sclerosis, etc.), bone/joint disorders (e.g., osteoporosis, osteoarthritis, chronic articular rheumatism, etc.), renal disorders (e.g., ischemic acute renal failure, hemolytic-uremic syndrome, acute tubular necrosis, hydronephrosis, glomerulonephritis, diabetic nephropathy, renal transplant rejection, etc.), liver diseases (e.g., viral hepatitis, alcoholic hepatitis, etc.), skin disorders, myelodysplastic diseases (e.g., aplastic anemia, etc.), autoimmune diseases (e.g., systemic lupus erythematosus, atopic dermatitis, etc.), cancerous diseases (e.g., breast cancer, testicular tumor, ovarian cancer, esophageal cancer, lung cancer, renal cancer, liver cancer, non-small-cell lung cancer, prostate cancer, gastric cancer, bladder cancer, uterocervical cancer, colon cancer, rectal cancer, pancreatic cancer, thymoma, etc.), metabolic diseases (e.g., diabetes mellitus, hyperlipemia, arteriosclerosis, etc.) or inflammatory diseases (e.g., pituitary tumor, thyroiditis, peritonitis, Crohn's disease, ulcerative colitis, nodular erythema, etc.).

(Screening Kit for Cell Protecting Agent)

The present invention provides a screening kit, which can be used advantageously for the screening method described above, in particular, a screening kit for the cell protecting agent showing the Hsp90 binding activity and the heat shock protein expression-inducing activity but showing no Hsp90 client protein degradation-promoting activity.

An example of the screening kit is a kit comprising (1) Hsp90, (2) a reagent for measurement of the heat shock protein expression-inducing activity, (3) the imidazothiazine derivative and (4) a reagent for quantification of the Hsp90 client protein. Hsp90 may be immobilized. The heat shock protein is not particularly limited and preferably is one or more selected from the group consisting of Hsp40, Hsp70 and Hsp90. The reagent for measurement of the heat shock protein expression-inducing activity includes, for example, a reagent for quantification or detection of a heat shock protein or mRNA encoding the heat shock protein. Specific examples include an antibody against a heat shock protein, a reagent enclosed in an ELISA kit, a reagent for mRNA measurement, a reagent for reporter assay using a heat shock element, and the like. The imidazothiazine derivative may be immobilized. The Hsp90 client protein is not particularly limited and is preferably one or more proteins selected from the group consisting of a glucocorticoid receptor, an Akt and a cycline dependent kinase 4. The reagent for quantification of the Hsp90 client protein is preferably an antibody against the Hsp90 client protein. Where the screening method is a method using a cell capable of expressing a protein, preferably the screening kit used therefor further comprises (5) a cell capable of expressing a heat shock protein and (6) a cell capable of expressing the Hsp90 client protein.

Another example of the screening kit of the present invention is a kit comprising (1) the Hsp90/HSF-1 complex, (2) Hsp90, (3) a reagent for quantification of Hsp90, (4) the imidazothiazine derivative and (5) a reagent for quantification of the Hsp90 client protein. The reagent for quantification of Hsp90 is preferably an antibody against Hsp90. Where the screening method is a method using a cell capable of expressing a protein, preferably the screening kit used therefor further comprises (6) a cell capable of expressing the Hsp90 client protein.

(Substance Obtained Using the Screening Method or the Screening Kit)

The present invention provides a substance obtained by using the screening method or screening kit described above, which shows the Hsp90 binding activity and the heat shock protein expression-inducing activity and has no Hsp90 client protein degradation-promoting activity. The substance may be, for example, a peptide, protein, non-peptide compound, synthetic compound, antibody, nucleic acid, vaccine, fermentation product, cell extract, plant extract, animal tissue extract, plasma, etc. The substance may also be in the form of salt of a peptide, protein, non-peptide compound or synthetic compound. The substance can be used as a cell protecting agent or medicament as it is. The substance can also be used as a cell protecting agent or medicament in the form of a mixture with other ingredients.

The substance obtained using the screening method or screening kit according to the present invention includes the imidazothiazine derivative of formula (I) described above. An example of the imidazothiazine derivative is N-[(1Z)-5,6-dimethyl-3-oxo-8-[(4,4,5,5,5-pentafluoropentyl)sulfanyl]-2,3-dihydro-1H-imidazo[5,1-c][1,4]thiazin-1-ylidene]-4-methylbenzenesulfonamide.

Where the step (1) in the screening method of the present invention involves measuring the inhibitory activity of a test compound against the binding property of Hsp90 to an imidazothiazine derivative and Compound of formula (I) described above or its salt is employed as the imidazothiazine derivative, the imidazothiazine derivative per se or its salt used in the screening method is excluded from "the substance obtained by the screening method or screening kit of the present invention."

(Cell Protecting Agent and Medicament)

The present invention provides a cell protecting agent comprising the substance obtained by the described above screening method or screening kit of the present invention, which shows the Hsp90 binding activity and the heat shock protein expression-inducing activity and has no Hsp90 client protein degradation-inducing activity, as well as a medicament comprising the cell protecting agent.

The cell protecting agent and medicament described above is useful as an agent for the prevention/treatment of various diseases, especially diseases associated with organ injuries and inflammation. These diseases include, for example, heart diseases (e.g., myocardiopathy, heart failure, angina pectoris, myocardial infarction, etc.), neurological disorders (e.g., Parkinson's disease, Alzheimer's disease, triplet repeat disease, prion disease, amyotrophic lateral sclerosis cerebellar degeneration, retinitis pigmentosa, etc.), brain diseases (e.g., cerebral infarction, etc.), central neuron infectious diseases (e.g., HIV encephalitis, bacterial meningitis, etc.), traumatic injuries (e.g., spinal cord injury, brain damage, etc.), demyelinating diseases (e.g., multiple sclerosis, etc.), bone/joint disorders (e.g., osteoporosis, osteoarthritis, chronic articular rheumatism, etc.), renal disorders (e.g., ischemic acute renal failure, hemolytic-uremic syndrome, acute tubular necrosis, hydronephrosis, glomerulonephritis, diabetic nephropathy, renal transplant rejection, etc.), liver diseases (e.g., viral hepatitis, alcoholic hepatitis, etc.), skin disorders, myelodysplastic diseases (e.g., aplastic anemia, etc.), autoimmune diseases (e.g., systemic lupus erythematosus, atopic dermatitis, etc.), cancerous diseases (e.g., breast cancer, testicular tumor, ovarian cancer, esophageal cancer, lung cancer, renal cancer, liver cancer, non-small-cell lung cancer, prostate cancer, gastric cancer, bladder cancer, uterocervical cancer, colon cancer, rectal cancer, pancreatic cancer, thymoma, etc.), metabolic diseases (e.g., diabetes mellitus, hyperlipemia, arteriosclerosis, etc.) or inflammatory diseases (e.g., pituitary tumor, thyroiditis, peritonitis, Crohn's disease, ulcerative colitis, nodular erythema, etc.).

The cell protecting agent and medicament described above can be formulated according to known methods, and orally or parenterally administered to a mammal (e.g., human, monkey, etc.) in a form as an agent for the prevention/treatment of the above diseases. Specifically, the compound described above may be blended with a pharmaceutically acceptable carrier, which may be orally administered in the form of a tablet, pill, granule, capsule, syrup, emulsion, suspension, etc., or parenterally including intravenously, subcutaneously and intramuscularly administered in the form of an injection, suppository, sublingual tablet, etc. Alternatively, the compound may also be administered sublingually, subcutaneously, intramuscularly, etc. in the form of a sustained release preparation such as a sublingual tablet, microcapsule, etc.

The pharmaceutically acceptable carrier described above includes various organic or inorganic carrier materials conventionally used as materials for pharmaceutical preparations, and is formulated as an excipient, a lubricant, a binder, a disintegrating agent, a solvent, a solution aid, a suspending agent, an isotonic agent, a buffer, a soothing agent, etc. If necessary, additives for pharmaceutical preparations such as an antiseptic, an antioxidant, a coloring agent, a sweetener, etc. may also be used.

A dose of the active ingredient (the substance obtained by the screening method or screening kit described above, which shows the Hsp90 binding activity and the heat shock protein expression-inducing activity and has no Hsp90 client protein degradation-inducing activity) contained in the pharmaceutical composition described above may vary depending on the severity of conditions; the age, sex and weight of the subject to be administered; the timing and interval of administration, the property, formulation and type of a pharmaceutical preparation; type of active ingredients, etc., without limitation. When the pharmaceutical composition is used for the treatment of, e.g., heart failure, the active ingredient may be administered to an adult generally in a daily dose of approximately 0.1 to 100 mg, preferably approximately 1.0 to 50 mg, and more preferably approximately 1.0 to 20 mg.

Hereinafter, the screening method of the present invention is described in more detail.

REFERENCE EXAMPLE 1

1. Preparation of Test Compound

The reactions (i) to (v) below were carried out to synthesize as a test compound an imidazothiazine derivative (name of the compound: N-[(1Z)-5,6-dimethyl-3-oxo-8-[(4,4,5,5,5-pentafluoropentyl)sulfanyl]-2,3-dihydro-1H-imidazo[5,1-c][1,4]thiazin-1-ylidene]-4-methylbenzenesulfonamide, hereinafter referred to as "compound A").

(i) Synthesis of N-[(4Z)-5-(dichloromethylene)-2-oximidazolidin-4-ylidene]-4-methylbenzenesulfonamide After 2-amino-3,3-dichloroacrylonitrile (31.9 g, 0.233 mol, manufactured by Junsei Chemical Co., Ltd.) was dissolved in diethyl ether (300 ml, hereinafter sometimes abbreviated as ether), p-toluenesulfonyl isocyanate (36.0 ml, 0.233 mol, purity of 98%, manufactured by Tokyo Chemical Industry Co., Ltd.) was dropwise added to the solution while stirring at room temperature. The mixture was stirred at room temperature for further 14 hours. The formed precipitate was filtrated, washed with diethyl ether and then dried to give light yellow powders of the title compound.

$^1$H NMR (CDCl$_3$-DMSO-d6=9:1): δ 2.44 (3H, s), 7.34 (2H, d, J=8.2 Hz), 7.90 (2H, d, J=8.2 Hz), 8.19 (1H, brs), 10.2 (1H, br).

Elemental analysis: as C$_{11}$H$_9$N$_3$O$_3$SCl$_2$
Calcd. (%): C, 39.54; H, 2.71; N, 12.57; S, 9.60; Cl, 21.22.
Found (%): C, 39.62; H, 2.48; N, 12.66; S, 9.63; Cl, 21.00.

(ii) Synthesis of ethyl 3-[[(5Z)-5-[[(4-methylphenyl)sulfonyl]imino]-2-oximidazolidin-4-ylidene](sulfanyl)methylsulfanyl]propanoate Potassium carbonate (65.8 g, 0.476 mol) and N,N-dimethylformamide (450 ml, hereinafter sometimes abbreviated as DMF) were added to N-[(4Z)-5-(dichloromethylene)-2-oxoimidazolidin-4-ylidene]-4-methylbenzenesulfonamide (45.5 g, 0.136 mol) synthesized in (i) described above. Ethyl 3-mercaptopropionate (35.9 ml, 0.272 mol) was dropwise added to the mixture over about 2 hours while stirring at room temperature. The reaction mixture was stirred at room temperature for further 12 hours and further stirred at 80° C. for 7 hours. After the reaction solution was concentrated to dryness, 2N hydrochloric acid (340 ml) and methanol (100 ml) were added to the residue and mixed. The formed precipitate was filtrated, washed with 50% methanol-water and ethanol and then dried to give orange brownish powders of the title compound.

$^1$H NMR (DMSO-d6): δ 1.18 (3H, t, J=7.1 Hz), 2.33 (3H, s), 2.63 (2H, t, J=7.1 Hz), 3.30 (1H, s), 3.32 (2H, t, J=7.1 Hz), 4.07 (2H, q, J=7.1 Hz), 7.28 (2H, d, J=8.1 Hz), 7.74 (2H, d, J=8.1 Hz), 8.75 (1H, brd, J=2 Hz), 9.61 (1H, brs).

Elemental analysis: as $C_{21}H_{27}N_3O_7S_3$
Calcd. (%): C, 47.62; H, 5.14; N, 7.93; S, 18.16.
Found (%): C, 47.51; H, 4.84; N, 8.19; S, 18.12.

(iii) Synthesis of ethyl 3-[[(1Z)-5,6-dimethyl-1-[[(4-methylphenyl)sulfonyl]imino]-3-oxo-2,3-dihydro-1H-imidazo[5,1-c][1,4]thiazin-8-yl]sulfanyl]propanoate After ethyl 3-[[(5Z)-5-[[(4-methylphenyl)sulfonyl]imino]-2-oximidazolidin-4-ylidene](sulfanyl) methylsulfanyl]propanoate (40 g, purity of about 50%, about 43 mmol) synthesized in (ii) described above was dissolved in THF (600 ml), 3-chloro-2-butanone (9.1 ml, 86 mmol) and triethylamine (35.8 ml, 0.258 mol) were added to the solution. The mixture was stirred at room temperature for 1.5 hours and then heated to reflux for 8 hours. The reaction solution was concentrated and the residue was diluted with ethyl acetate (600 ml). The dilution was washed with 2% sodium hydrogencarbonate aqueous solution, water, 0.1N hydrochloric acid, water and then saturated salt solution, dried over sodium sulfate and concentrated to dryness under reduced pressure to give brown oil containing the title compound.

The brown oil described above was dissolved in toluene (580 ml) and acetic anhydride (11.4 ml) and p-toluenesulfonic acid monohydrate (8.98 g, 47 mmol) was added to the solution. The mixture was heated at 100° C. for 2 hours while stirring. The reaction solution was concentrated and the residue was diluted with ethyl acetate (700 ml). The dilution was washed 4 times with water and with saturated salt solution, and dried over sodium sulfate. The solvent was removed by distillation under reduced pressure. Methanol was added to the residue and the formed precipitate was filtrated, washed with methanol and dried to give red purple powders of the title compound.

$^1$H NMR (CDCl$_3$): δ 1.27 (3H, t, J=7.2 Hz), 1.79 (3H, brq, J=0.8 Hz), 2.26 (3H, brq, J=0.8 Hz), 2.42 (3H, s), 2.70 (2H, t, J=7.5 Hz), 3.20 (2H, t, J=7.5 Hz), 4.17 (2H, q, J=7.2 Hz), 7.29 (2H, d, J=8.3 Hz), 7.84 (2H, d, J=8.3 Hz), 9.61 (1H, br).

Elemental analysis: as $C_{20}H_{23}N_3O_5S_3$
Calcd. (%): C, 49.88; H, 4.81; N, 8.72; S, 19.97.
Found (%): C, 49.78; H, 5.03; N, 8.68; S, 20.00.

(iv) N-[(1Z)-8-Mercapto-5,6-dimethyl-3-oxo-2,3-dihydro-1H-imidazo[5,1-c][1,4]thiazin-1-ylidene]-4-methylbenzenesulfonamide was synthesized by the following procedures After ethyl 3-[[(1Z)-5,6-dimethyl-1-[[(4-methylphenyl)sulfonyl]imino]-3-oxo-2,3-dihydro-1H-imidazo[5,1-c][1,4]thiazin-8-yl]sulfanyl]propanoate (5.00 g, 10.4 mmol) synthesized in (iii) described above was dissolved in THF (50 ml) and methanol (50 ml), potassium hydroxide (2.74 g, 41.5 mmol) was added to the solution. The mixture was stirred at room temperature for 45 minutes. 1N Hydrochloric acid (42 ml) was added to and mixed with the reaction solution, and the mixture was stirred at room temperature for 30 minutes. The formed precipitate was filtrated, washed with 50% methanol-water and dried to give red powders of the title compound.

$^1$H NMR (CDCl$_3$-DMSO-d6=9:1): δ 1.81 (3H, s), 2.42 (3H, d, J=0.5 Hz), 2.45 (3H, s), 7.35 (2H, d, J=8.1 Hz), 7.88 (21-1, d, J=8.3 Hz), 12.82 (2H, br).

Elemental analysis: as $C_{15}H_{15}N_3O_3S_3$
Calcd. (%): C, 47.22; H, 3.96; N, 11.01; S, 25.22.
Found (%): C, 47.20; H, 3.90; N, 10.73; S, 25.19.

(v) Synthesis of N-[(1Z)-5,6-dimethyl-3-oxo-8-[(4,4,5,5,5-pentafluoropentyl)sulfanyl]-2,3-dihydro-1H-imidazo[5,1-c][1,4]thiazin-1-ylidene]-4-methylbenzenesulfonamide (Compound A)

v-1.
4,4,5,5,5-Pentafluoropentyl methanesulfonate was synthesized to provide as a reaction reagent. First, methanesulfonyl chloride (0.652 ml, 8.42 mmol) and triethylamine (1.57 ml, 11.2 mmol) were sequentially added to a solution of 4,4,5,5,5-pentalluoro-1-pentanol (1.00 g, 5.61 mmol) in tetrahydrofuran (20.0 ml) under ice cooling. After the reaction mixture was stirred at room temperature for 3 hours, 1N hydrochloric acid was added to the mixture followed by extraction with ethyl acetate. The extract was washed with water and dried (with MgSO$_4$). The solvent was then removed by distillation under reduced pressure to give the title compound as oily substance.

IR absorption spectrum (IR) (KBr) ν: 3031, 2946, 912, 743 cm$^{-1}$.

$^1$H-NMR (CDCl$_3$): δ 1.98-2.35 (4H, m), 3.05 (3H, s), 4.32 (211, t, J=5.6 Hz).

v-2:
A solution of 4,4,5,5,5-pentafluoropentyl methanesulfonate (24.0 g, 93.7 mmol) obtained in (v-1) described above in N,N-dimethylformamide (100 ml) was added to a suspension of N-[(1Z)-8-mercapto-5,6-dimethyl-3-oxo-2,3-dihydro-1H-imidazo[5,1-c][1,4]thiazin-1-ylidene]-4-methylbenzenesulfonamide (29.8 g, 78.1 mmol) obtained in (iv) described above and potassium carbonate (16.2 g, 0.117 mol) in N,N-dimethylformamide (400 ml). After the reaction mixture was heated at 80° C. for 2 hours, 1N hydrochloric acid was added to the mixture, followed by extraction with ethyl acetate. The extract was washed with water and dried (with MgSO$_4$). The solvent was then removed by distillation under reduced pressure to give Compound A as dark red crystals. Recrystallization from ethyl acetate-diethyl ether gave Compound A as dark red crystals showing melting point at 190-192° C.

IR absorption spectrum (IR) (KBr) ν: 3208, 2934, 1753, 1663, 1624, 1566, 1497 cm$^{-1}$.

$^1$H-NMR (CDCl$_3$): δ 1.79 (3H, d, J=1.0 Hz), 1.90-2.22 (4H, m), 2.27 (3H, d, J=1.2 Hz), 2.42 (3H, s), 3.01 (2H, t, J=6.8 Hz), 7.29 (2H, d, J=8.0 Hz), 7.84 (2H, d, J=8.4 Hz), 9.62 (1H, bs).

Elemental analysis: as $C_{20}H_{20}N_3O_3S_3F_5$
Calcd. (%): C, 44.35; H, 3.72; N, 7.76; S, 17.76.
Found (%): C, 44.32; H, 3.69; N, 7.44; S, 17.67.

Depending upon purposes, a solution of compound A dissolved in N,N-dimethylformamide (DMF) was diluted with an appropriate buffer solution and used for the measurement method described in EXAMPLES.

2. Reference Compound

Geldanamycin (([18S-(4E,5Z,8R*,9R*,10E,12R*,13S*, 14R*,16S*)]-9-[(aminocarbonyl)oxy]-13-hydroxy-8,14,19-trimethoxy-4,10,12,16-tetramethyl-2-azabicyclo[16.3.1.]docosa-4,6,10,18,21-pentan-3,20,22-trion), which is a known Hsp90 inhibitor, was used as a reference compound. "Geldanamycin from *Streptomyces hygroscopicus*" available from Sigma Inc. was used as geldanamycin (herein referred to as "GA").

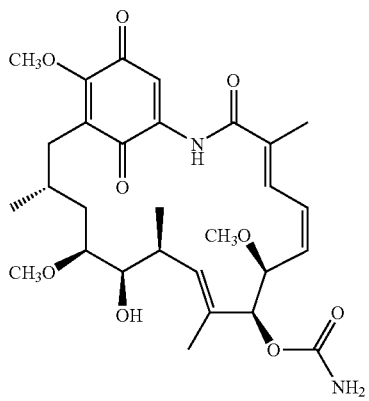

REFERENCE EXAMPLE 2

An immobilized imidazothiazine derivative to be used in EXAMPLE 1 was prepared.
(1) Preparation of Imidazothiazine Derivative The reactions (i) to (iv) below were carried out to synthesize an imidazothiazine derivative wherein carboxyl was introduced at the terminus (5-[[(1Z)-5,6-dimethyl-3-oxo-1-([[4-(trifluoromethyl)phenyl]sulfonyl]imino)-2,3-dihydro-1H-imidazo[5,1-c][1,4]thiazin-8-yl]sulfanyl]pentanoic acid, hereinafter referred to as "Compound B").

(i) Synthesis of ethyl 5-[[(1Z)-5,6-dimethyl-1-[[(4-methylphenypsulfonyl]imino]-3-oxo-2,3-dihydro-1H-imidazo[5,1-c][1,4]thiazin-8-yl]sulfanyl]pentanoate A solution of ethyl 5-bromovalerate (0.259 ml, 1.57 mmol) in N,N-dimethylformamide (5.00 ml) was added to a suspension of N-[(1Z)-8-Mercapto-5,6-dimethyl-3-oxo-2,3-dihydro-1H-imidazo[5,1-c][1,4]thiazin-1-ylidene]-4-methylbenzenesulfonamide (500 mg, 1.31 mmol) obtained in (iv) of REFERENCE EXAMPLE 1 and potassium carbonate (272 mg, 1.97 mmol) in N,N-dimethylformamide (5.00 ml). After the reaction mixture was heated at 80° C. for 30 minutes, 1N hydrochloric acid was added to the mixture, followed by extraction with ethyl acetate. The extract was washed with water and dried (with $MgSO_4$). The solvent was removed by distillation under reduced pressure to synthesize the title compound. Recrystallization from ethyl acetate-diethyl ether gave dark red crystals showing a melting point at 162-164° C.

IR absorption spectrum (IR) (KBr) ν: 3221, 2980, 2936, 1732, 1663, 1564 cm$^{-1}$. $^1$H-NMR (CDCl$_3$): δ 1.27 (3H, t, J=7.2 Hz), 1.67-1.82 (4H, m), 1.79 (3H, d, J=1.0 Hz), 2.26 (3H, d, J=1.2 Hz), 2.28-2.38 (2H, m), 2.42 (3H, s), 2.88-2.98 (2H, m), 4.14 (2H, q, J=7.2 Hz), 7.29 (2H, d, J=8.0 Hz), 7.85 (2H, d, J=8.4 Hz), 9.61 (1H, bs).

Elemental analysis: as $C_{22}H_{27}N_3O_5S_3$
Calcd. (%): C, 51.85; H, 5.34; N, 8.24; S, 18.87.
Found (%): C, 51.68; H, 5.29; N, 8.16; S, 18.42.

(ii) Synthesis of ethyl 5-[(1-amino-5,6-dimethyl-3-oxo-3H-imidazo[5,1-c][1,4]thiazin-8-yl)sulfanyl]pentanoate A suspension of ethyl 5-[[(1Z)-5,6-dimethyl-1-[[(4-methylphenyl)sulfonyl]imino]-3-oxo-2,3-dihydro-1H-imidazo[5,1-c][1,4]thiazin-8-yl]sulfanyl]pentanoate (1.34 g, 2.63 mmol) obtained in (i) described above and ammonium formate (1.75 g, 26.3 mmol) in ethanol (26.0 ml) was heated at 80° C. for 17 hours. Then, water was added to the mixture, which was extracted with ethyl acetate. After the extract was washed with water and dried (with $MgSO_4$), the solvent was removed by distillation under reduced pressure. The residue was applied to silica gel column chromatography and eluted with n-hexane-ethyl:acetate (10:1, v/v) to give the title compound as dark red crystals. Recrystallization from ethyl acetate-diethyl ether gave the dark red crystals showing a melting point at 92.0-94.0° C.

IR absorption spectrum (IR) (KBr) ν: 3405, 3283, 3115, 2978, 2936, 1723, 1634, 1665, 1537 cm$^{-1}$.
$^1$H-NMR (CDCl$_3$): δ 1.26 (3H, d, J=6.9 Hz), 1.70-1.84 (4H, m), 1.74 (3H, s), 2.26 (3H, s), 2.32-2.40 (2H, m), 2.88-2.98 (2H, m), 4.14 (2H, q, J=6.9 Hz), 7.51 (2H, bs).

Elemental analysis: as $C_{15}H_{21}N_3O_3S_2$
Calcd. (%): C, 49.92; H, 5.87; N, 11.64; S, 17.77.
Found (%): C, 49.94; H, 5.79; N, 11.41; S, 17.72.

(iii) Synthesis of ethyl 5-[[(1Z)-5,6-dimethyl-3-oxo-1-([[4-(trifluoromethyl)phenyl]sulfonyl]imino)-2,3-dihydro-1H-imidazo[5,1-c][1,4]thiazin-8-yl]sulfanyl]pentanoate A solution of ethyl 5-[(1-amino-5,6-dimethyl-3-oxo-3H-imidazo[5,1-c][1,4]thiazin-8-yl)thio]pentanoate (1.02 g, 2.87 mmol) obtained in (ii) described above in tetrahydrofuran (5.00 ml) was added to a suspension of sodium hydride (230 mg, 5.74 mmol) (60% oily) in tetrahydrofuran (10.0 ml) and the mixture was stirred under ice cooling for 5 minutes. A solution of 4-(trifluoromethyl)benzenesulfonyl chloride (1.40 g, 5.74 mmol) in tetrahydrofuran (5.00 ml) was added to the mixture, followed by further stirring at room temperature for an hour. 1N Hydrochloric acid was added to the reaction mixture and the mixture was extracted with ethyl acetate. After the extract was washed with water and dried (with $MgSO_4$), the solvent was removed by distillation under reduced pressure to give the title compound as dark red crystals. Recrystallization from ethyl acetate-diethyl ether gave the dark red crystals showing a melting point at 146-148° C.

IR absorption spectrum (IR) (KBr) ν: 3235, 2984, 2936, 1759, 1738, 1663, 1620, 1559 cm$^{-1}$.
$^1$H-NMR (CDCl$_3$): δ 1.26 (3H, d, J=7.2 Hz), 1.70-1.78 (4H, m), 1.80 (3H, d, J=1.2 Hz), 2.28 (3H, d, J=0.9 Hz), 2.31-2.38 (2H, m), 2.94-3.00 (2H, m), 4.14 (2H, q, J=7.2 Hz), 7.77 (2H, d, J=8.7 Hz), 8.11 (2H, d, J=9.0 Hz), 9.61 (1H, bs).

Elemental analysis: as $C_{22}H_{24}N_3O_5S_3F_3$
Calcd. (%): C, 46.88; H, 4.29; N, 7.46; S, 17.07.
Found (%): C, 46.86; H, 4.17; N, 7.62; S, 17.16.

(iv) Synthesis of 5-[[(1Z)-5,6-dimethyl-3-oxo-1-([[4-(trifluoromethyl)phenyl]sulfonyl]imino)-2,3-dihydro-1H-imidazo[5,1-c][1,4]thiazin-8-yl]sulfanyl]pentanoic acid (Compound B)

An aqueous 1N hydrochloric acid solution (5.59 ml) was added to a solution of ethyl 5-[[(1Z)-5,6-dimethyl-3-oxo-1-([[4-(trifluoromethyl)phenyl]sulfonyl]imino)-2,3-dihydro-1H-imidazo[5,1-c][1,4]thiazin-8-yl]sulfanyl]pentanoate (1.05 g, 1.86 mmol) obtained in (iii) described above in ethanol (10.0 ml) and tetrahydrofuran (10.0 ml). After the reaction mixture was stirred at room temperature for an hour, the solvent was removed by distillation under reduced pressure. To the residue, 1N hydrochloric acid was added and the mixture was extracted with ethyl acetate. After the extract was washed with water and dried (with $MgSO_4$), the solvent was removed by distillation under reduced pressure to give the title compound (747 mg, 75%) as dark red crystals. Recrystallization from ethyl acetate-diethyl ether gave Compound B as dark red crystals showing a melting point at 191-193° C.

IR absorption spectrum (IR) (KBr) ν: 3700-2400, 3125, 2928, 1725, 1663, 1599, 1557 $cm^{-1}$.

$^1$H-NMR ($CDCl_3$): δ 1.70-1.83 (4H, m), 1.80 (3H, d, J=1.2 Hz), 2.28 (3H, d, J=1.2 Hz), 2.37-2.45 (2H, m), 2.94-3.02 (2H, m), 7.77 (2H, d, J=8.1 Hz), 8.11 (2H, d, J=8.4 Hz), 9.69 (1H, bs).

Elemental analysis: as $C_{20}H_{20}N_3O_5S_3F_3$

Calcd. (%): C, 44.85; H, 3.76; N, 7.85; S, 17.96.

Found (%): C, 44.39; H, 4.04; N, 7.83; S, 17.66.

(2) Immobilization of Imidazothiazine Derivative

The imidazothiazine derivative (Compound B) was immobilized by the following procedures. First, Compound B was dissolved in 85% N,N-dimethylformamide (DMF) in a concentration of 100 mM. Next, 20 mg of 1-ethyl-3-(3-dimethylaminopropyl)carbodiimide hydrochloride (EDC) and 1 ml of AF-Amino Toyopearl 650 (manufactured by Toso Co.) were added to 2 ml of the solution above. After pH was adjusted to 5.0, the mixture was stirred at room temperature for a day to react the carboxyl group of Compound B with the amino group of AF-Amino Toyopearl 650. After completion of the reaction, the AF-Amino Toyopearl 650 carrier was washed with 85% DMF, and 570 μl of 0.2 M sodium acetate and 285 μl of glacial acetic acid were added thereto. After the mixture was maintained at 0° C. for 30 minutes, 285 μl of glacial acetic acid was added thereto and the mixture was kept at 25° C. for further 30 minutes. This carrier was repeatedly washed with water and 0.1 N NaCl and then equilibrated with Binding Buffer, which was used as the immobilized imidazothiazine derivative (hereinafter referred to as "immobilized Compound B") in EXAMPLES below.

EXAMPLES

Example 1

In an embodiment of the step (1) in the screening method of the invention, the steps of measuring and comparing (i) the binding level of an immobilized imidazothiazine derivative to Hsp90 in the absence of a test compound and (ii) the binding level of an immobilized imidazothiazine derivative to Hsp90 in the presence of a test compound, were performed as follows.

(1) Preparation of His-hHsp90α

Purified human Hsp90α protein (His-hHsp90α) tagged with histidine at the N terminus through using *Escherichia coli* was employed as Hsp90. His-hHsp90a was prepared as follows.

First, the Hsp90α coding region was amplified from a human skeletal complementary DNA (cDNA) library (Clontech, Inc.) by polymerase chain reaction (PCR). For the cDNA amplification of human Hsp90α, a sense strand (SEQ ID NO: 1) which coincided with the N terminus of human Hsp90α containing the BamHI cleavage site at the 5' end and an antisense strand (SEQ ID NO: 2) which coincided with the C terminus of human Hsp90α containing the SalI cleavage site at the 5' end were used. After the amplified human Hsp90α was cleaved with BamHI and SalI, the resulting fragment was inserted between the BamHI cleavage site and the SalI cleavage site in pET28b (Novagen) to give pET28b-hHsp90a. The hHsp90αcDNA sequence in the plasmid obtained was confirmed using a DNA Sequencing System (Applied Biosystems, Inc.).

pET28b-hHsp90α was transformed into *Escherichia coli* BL21 (DE3) (Novagen) and then inoculated into LB medium with ampicillin followed by shaking culture at 37° C. overnight. The transformant was transferred to another medium with the same components in a concentration of 1%. After incubation at 37° C. for about 2.5 hours, 1 mM isopropyl-1-thio-β-D-galactopyranoside (IPTG) was added and incubation was continued for further 4 hours at 37° C. to induce expression of the His-hHsp90α protein. After completion of the incubation, *Escherichia coli* was recovered and 10 ml of 0.1% NP40-containing buffer (20 mM Tris-HCl (pH 7.9)/500 mM NaCl/5 mM imidazole) per a cell volume obtained from 100 ml of the culture medium was added, followed by ultra-sonication. This sonicated cell lysate was centrifuged at 10,000 rpm for 15 minutes and the supernatant was recovered. The supernatant was applied to a nickel column to obtain the His-hHsp90α protein.

(2) Method for Measurement of Binding Property of Test Compound to Hsp90

Immobilized Compound B prepared in REFERENCE EXAMPLE 2 was used as the immobilized imidazothiazine derivative. First, 10 μg of His-hHsp90α was reacted with a test compound of various concentrations in 0.2 ml of a binding buffer (10 mM Tris-HCl, pH 7.5, 20% glycerol, 1 mM EDTA, 500 mM NaCl and 1 mM DTT) containing 0.5% DMF for 30 minutes. Next, 10 μl of the immobilized Compound B was added to the reaction mixture. The mixture was kept at room temperature for 40 minutes while stirring to bind His-hHsp90α to the immobilized Compound B. After completion of the reaction, the immobilized compound B was washed 5 times with 0.2 ml of the binding buffer to wash and remove His-hHsp90α unbound to the immobilized Compound B. Subsequently, the immobilized Compound B was equally mixed with a sample buffer (Tris-SDS-ME Sample Buffer; manufactured by Daiichi Pure Chemicals Co., Ltd.). The mixture was heat-treated at 95° C. for 5 minutes to elute the His-hHsp90α bound to the immobilized Compound B. Then, SDS polyacrylamide electrophoresis was performed using Multigel (manufactured by Daiichi Pure Chemicals Co., Ltd.). After completion of the electrophoresis, the polyacrylamide gel was silver-stained to detect the His-hHsp90α bound to the immobilized Compound B.

(3) Results of Measurement

Compound A as a test compound dose-dependently decreased the binding level of the His-hHsp90α protein to the immobilized Compound B. On the other hand, reference compound GA had no effect at concentrations of 50 μM or less (FIG. 1). Accordingly, it is considered that Compound A would strongly bind to the same site in His-hHsp90α as the immobilized Compound B but the affinity of GA to the binding site is low.

It was shown that the test compound (Hsp90 inhibitor) having the Hsp90 binding activity can be screened by this step.

Example 2

In another embodiment of the step (1) of the screening method according to the present invention, measuring and comparing (i) the binding level of immobilized Hsp90 to a labeled imidazothiazine derivative in the absence of a test compound and (ii) the binding level of immobilized Hsp90 to a labeled imidazothiazine derivative in the presence of a test compound were performed.

(1) Preparation of Immobilized Hsp90 Protein

Purified human Hsp90α protein (His2-hHsp90a) tagged with histidine at the N terminus through using *Escherichia coli* was employed as Hsp90. His2-hHsp90α was prepared as follows. First, the hHsp90α gene was excised from pET28b-hHsp90α using the BamHI cleavage site and the Bpu1102I cleavage site and inserted between the BamHI and the Bpu1102I cleavage sites in pET15b(Novagen) to obtain pET15b-hHsp90α.

pET15b-hHsp90α was transformed into *Escherichia coli* BL21 (DE3) (Novagen) and incubated in M-9 medium supplemented with ampicillin. After 1 mM of isopropyl-1-thio-β-D-galactopyranoside (IPTG) was added thereto, incubation was performed at 37° C. for 4 hours to induce expression of the His2-hHsp90α protein. After completion of the incubation, *Escherichia coli* was recovered and a buffer (50 mM Tris-HCl (pH 8.0)/5 mM EDTA/0.5 mM APMSF) was added thereto, followed by ultrasonication. This sonicated cell lysate was centrifuged at 39,800×G for 30 minutes and the supernatant was recovered. The supernatant was treated with 60% saturated ammonium sulfate at 4° C. for 15 hours to precipitate proteins, followed by centrifugation at 30,100×G for 30 minutes. The obtained precipitate was suspended in a buffer (20 mM Tris-HCl, pH 8.0, 300 mM NaCl and 10 mM imidazole). The suspension was applied to a nickel column to obtain the His2-hHsp90α protein. The obtained His2-hHsp90α was further purified on HPLC using a DEAE-5PW column and provided for use.

Next, 62.5 μg of Ysi (2-5 μm) copper his-tag SPA beads (manufactured by Amersham Biosciences Inc.) was mixed with 0.8 μg of the His2-hHsp90α protein in 100 μl of phosphate buffered saline (PBS) containing 0.025% Tween 20 and 100 μM DTT. The mixture was reacted overnight at 4° C. in a 96-well LumiNunc plate (manufactured by Nunc, Inc.). The above procedure gave immobilized Hsp90 in which the His2-hHsp90α protein was bound to Ysi (2-5 μm) copper his-tag SPA beads via histidine tag.

(2) Method for Measurement of Binding Property of Test Compound to Hsp90

Tritium-labeled Compound A (hereinafter sometimes referred to as [$^3$H]-Compound A) was used as the labeled imidazothiazine derivative. Various concentrations of a test compound (Compound A) and 40 nM tritium-labeled compound A were added to the described above plate containing immobilized Hsp90. After the mixture was allowed to stand at room temperature for 6 hours, the radioactivity of [$^3$H]-compound A bound to the His2-hHsp90α protein was counted in a microplate scintillator counter (manufactured by TopCount NXT; Packard).

The total binding level of [$^3$H]-compound A was determined by subtracting the level as non-specific binding that was obtained when Ysi (2-5 μm) copper his-tag SPA beads not immobilized with the His2-hHsp90α protein was reacted with 40 nM [$^3$H]-Compound A.

(3) Results of Measurement

Figure 2:
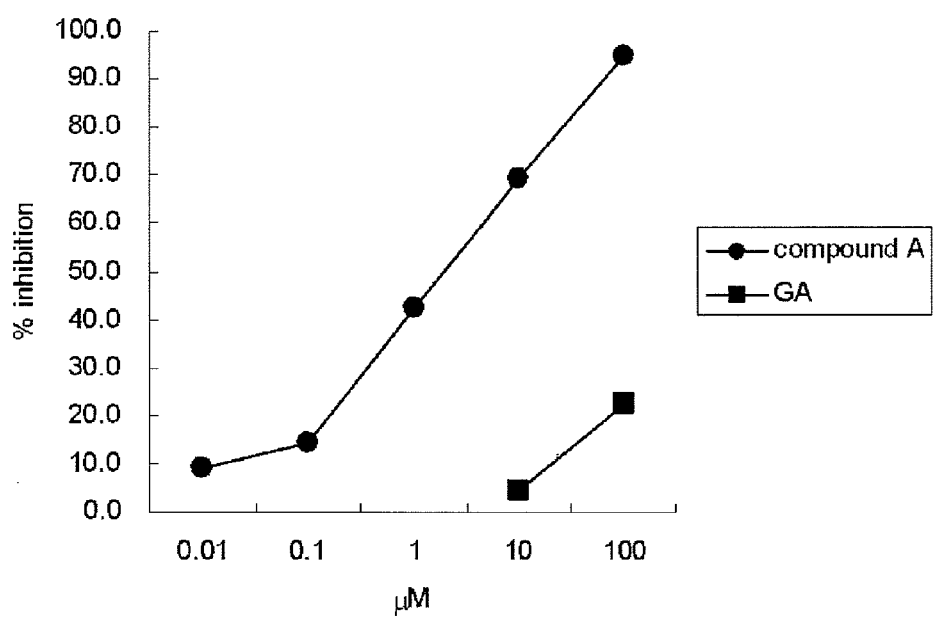
FIG. 2 is a graph showing the effects of a test compound (Compound A) and a reference compound (GA) on the binding of [$^3$H]-compound A to His2-hHsp90α protein.

Compound A which is a test compound dose-dependently decreased the binding level of the His2-hHsp90α protein to [$^3$H]-compound A but GA showed only a weak inhibitory activity of 30% or less at concentrations of 100 μM or less (FIG. 2). It is therefore considered that the affinity of GA to the Compound A-binding site in the Hsp-90 would be low.

According to this step, it is shown that a test compound having the binding property to Hsp90 (Hsp90 inhibitor) can be screened.

Example 3

In an embodiment of the step (2), the heat shock protein expression-inducing activity of a test compound was measured using a cell capable of expressing a heat shock protein. Hsp70 was used as the heat shock protein.

(1) Preparation of Cell Capable of Expressing Hsp70

Human normal articular chondrocytes (manufactured by Clonetics Corporation) were grown by monolayer culture in a growth medium for articular chondrocytes (CGM, manufactured by Clonetics Corporation) and then suspended to 2.2× $10^4$ cells/ml in a 1:1 mixture of Dulbecco's modified Eagle's medium/Ham F12 medium. The cell culture was inoculated into a 12-well plate (manufactured by Asahi Techno Glass Corporation) by 3 ml per each well, followed by incubation at 37° C. for a day under 5% $CO_2$.

(2) Method for Measurement of Hsp70 Expression-Inducing Activity of Test Compound The medium was exchanged to a fresh 1:1 mixture of Dulbecco's modified Eagle's medium/Ham F 12 medium, and a test compound and 10 ng/ml of IL-1β (manufactured by Genzyme Techne) were added to the medium, followed by incubation at 37° C. for 2 days under 5% $CO_2$. After completion of the incubation, the medium was washed once with phosphate-buffered saline (PBS), and 100 μl of a cell lysis buffer (10 mM Tris(hydroxymethyl)aminomethane, pH7.4, 150 mM NaCl, 1 mM EDTA.2Na, 1 mM EGTA, 0.5 mM (p-aminophenyl)methanesulfonyl fluoride hydrochloride, 200 μM sodium (3-glycerophosphate n-hydrate, 20 mM NaF, 2 mM sodium diphosphate decahydrate, 10 μg/ml aprotinin, 10 μg/ml leupeptin, 1% Triton X-100, 0.5% Nonidet P40, 0.1% SDS and 1 mM o-vanadate) was added thereto. The cell debris was scraped from the plate using a cell scraper, and this cell lysis buffer was recovered. The recovered cell lysis buffer was equally mixed with a sample buffer (Tris-SDS-ME Sample Buffer; manufactured by Daiichi Pure Chemicals Co., Ltd.). The mixture was heat-treated at 95° C. for 5 minutes and then subjected to SDS polyacrylamide electrophoresis using Multigel (manufactured by Daiichi Pure Chemicals Co., Ltd.).

After completion of the electrophoresis, the proteins in the gel were adsorbed onto a nitrocellulose membrane (Hybond-ECL; manufactured by Amersham Pharmacia Biotech Inc.) using HorizBlot (manufactured by Atto Co.). Each protein level was measured by western blotting using anti-Hsp70 antibody (manufactured by Transduction Laboratories) or anti-β-actin antibody (manufactured by Sigma, Inc.) as a primary antibody and horseradish peroxidase-labeled anti-mouse IgG antibody (manufactured by Kirkegaard & Perry Laboratories) as a secondary antibody. β-Actin was used to verify adsorption of the proteins onto the nitrocellulose membrane.

(3) Results of Measurement

Figure 3:
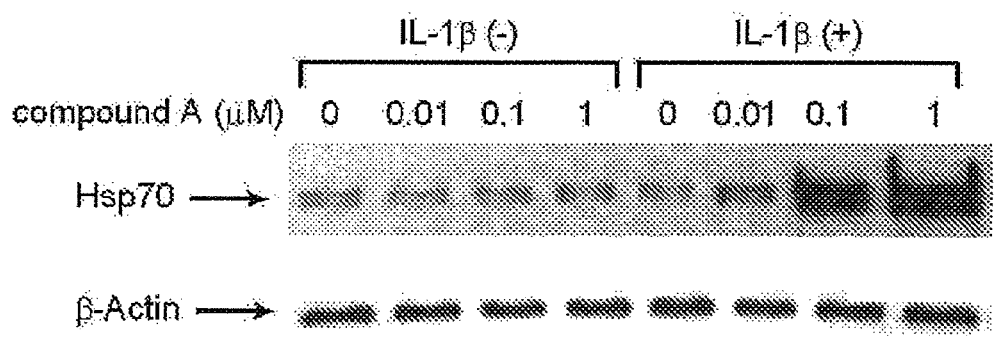
FIG. 3 is western blots showing the Hsp70 expression-inducing activities of a test compound (Compound A) and a reference compound (GA) in the presence of IL-1β stimulation.
Figure 3:
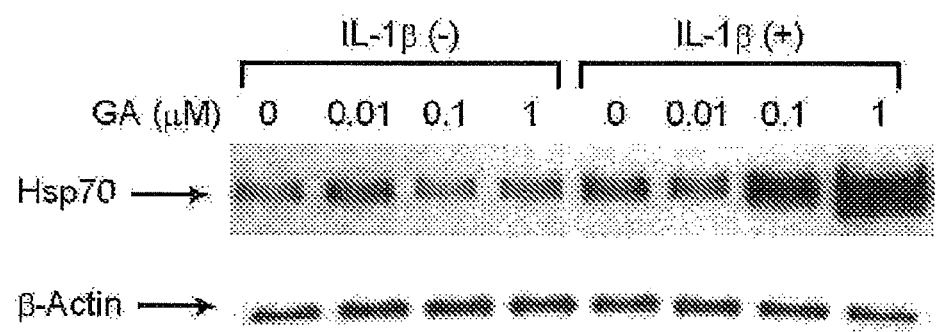

Both Compound A as the test compound and GA as the reference compound clearly increased the Hsp70 protein level in the presence of IL-1β stimulation (FIG. 3). These two compounds were considered almost equivalent in the Hsp70 expression-inducing activity.

According to this step, it was shown that the substance having the heat shock protein expression-inducing activity can be screened by measuring the heat shock protein expression-inducing activity of the test compound.

Example 4

In another embodiment of the step (2), the activity of a test compound to disrupt the Hsp90/HSF-1 complex was measured. The substance having the activity to disrupt Hsp90/HSF-1 complex is expected to show the heat shock protein expression-inducing activity.

(1) Preparation of Hsp90/HSF-1 Complex

Human normal articular chondrocytes (manufactured by Clonetics) were washed with PBS and dissolved in RIPA buffer solution (50 mM Tris-HCl, pH 8.0, 150 mM NaCl, 1% NP-40, 0.1% SDS and 0.5% deoxycholic acid) containing a proteinase inhibitor (Complete; Boehringer Mannheim). After the solution was centrifuged at 16,000×g for 10 minutes, the supernatant was used as the lysate containing the Hsp90/HSF-1 complex.

(2) Method for Measurement of Disrupting Activity against Hsp90/HSF-1 Complex

Next, 0.6 ml of the lysate was diluted to 2 mg/ml, 1 µM Compound A or buffer was added thereto, and the mixture was reacted for 30 minutes. After 30 µg of anti-Hsp90 antibody (SPA-840; manufactured by StressGen) or a control antibody (manufactured by Sigma, Inc.) was added thereto to react them for 30 minutes, 50 of protein A/G agarose (manufactured by Santa Cruz) was added thereto. The mixture was reacted at 4° C. for further 3 hours while stirring to adsorb the antibody onto the protein A/G agarose. Next, the beads were recovered by centrifugation, washed 7 times with RIPA buffer solution and mixed with the equal volume of a sample buffer (Tris-SDS-ME Sample Buffer; manufactured by Daiichi Pure Chemicals). After heat treatment at 95° C. for 5 minutes, the mixture was subjected to SDS polyacrylamide electrophoresis using Multigel (manufactured by Daiichi Pure Chemicals).

After completion of the electrophoresis, the proteins in the gel were adsorbed onto a nitrocellulose membrane (Hybond-ECL; manufactured by Amersham Pharmacia Biotech Inc.) using HorizBlot (manufactured by Atto Co.). Each protein level was measured by western blotting using anti-HSF-1 antibody (manufactured by StressGen) or anti-Hsp90 antibody (manufactured by Transduction Laboratories) as a primary antibody and horseradish peroxidase-labeled anti-rabbit IgG antibody (manufactured by Cell Signaling Technology) or horseradish peroxidase-labeled anti-mouse IgG antibody (manufactured by Kirkegasrd & Perry Laboratories) as a secondary antibody.

(3) Results of Measurement

Figure 4:
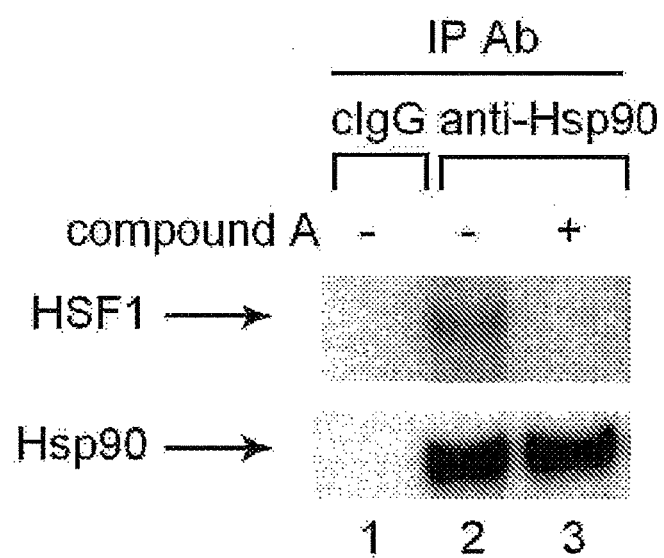
FIG. 4 is western blots showing that the test compound (Compound A) has disrupted the Hsp90/HSF-1 complex in the immunoprecipitation experiment.

When the control antibody was used during immunoprecipitation, the Hsp90 protein was not recovered from the lysate, nor was HSF-1 detected (FIG. 4, lane 1). On the other hand, when the anti-Hsp90 antibody was used during immunoprecipitation, Hsp90 was recovered from the lysate accompanied by coprecipitation of HSF-1 (FIG. 4, lane 2). These results reveal that the Hsp90/HSF-1 complex can be recovered from the lysate in this experiment system. Next, when Compound A was co-present upon recovery of the Hsp90/HSF-1 complex using the anti-Hsp90 antibody, Hsp90 was recovered from the lysate but the co-precipitation of HSF-1 was not observed (FIG. 4, lane 3). The foregoing results reveal that Compound A acts to disrupt the Hsp90/HSF-1 complex.

According to this step, it was shown that the test compound having the activity of disrupting the Hsp90/HSF-1 complex can be screened.

Example 5

In an embodiment of the step (3) according to the screening method of the present invention, the Hsp90 client protein degradation-inducing activity of a test compound was measured using a cell capable of expressing an Hsp90 client protein.

(1) Preparation of Cell Capable of Expressing Hsp90 Client Protein

Human normal articular chondrocytes were suspended to $0.5 \times 10^5$ cells/ml in a growth medium for articular chondrocytes. The cell culture was inoculated into a 6-well plate (manufactured by Falcon Co., Ltd.) by 2 ml per each well, followed by incubation at 37° C. for a day under 5% $CO_2$. The medium was exchanged to a 1:1 mixture of Dulbecco's modified Eagle's medium/Ham F12 medium, followed by further incubation at 37° C. for a day under 5% $CO_2$.

(2) Method for Measuring the Hsp90 Client Protein Degradation-Inducing Activity of Test Compound The test compound was added to the culture medium and the cells were further incubated for about 18 hours at 37° C. under 5% $CO_2$. After completion of the incubation, the cells were washed once with phosphate-buffered saline (PBS) and 200 µl of a cell lysate buffer (10 mM Tris(hydroxymethyl)aminomethane, pH 7.4, 150 mM NaCl, 1 mM EDTA.2Na, 1 mM EGTA, 0.5 mM (p-aminophenyl)methanesulfonyl fluoride hydrochloride, 200 µM sodium β-glycerophosphate n-hydrate, 20 mM NaF, 2 mM sodium diphosphate decahydrate, 10 µg/ml aprotinin, 10 µg/ml leupeptin, 1% Triton X-100, 0.5% Nonidet P40, 0.1% SDS and 1 mM o-vanadate) was added thereto. After the cell debris was scraped from the plate using a cell scraper, the cell lysate buffer was recovered. The recovered cell lysate buffer was mixed with the equal volume of a sample buffer (Tris-SDS-ME Sample Buffer; manufactured by Daiichi Pure Chemicals). The mixture was heat-treated at 95° C. for 5 minutes and subjected to SDS polyacrylamide electrophoresis using Multigel (manufactured by Daiichi Pure Chemicals).

After completion of the electrophoresis, the proteins in the gel were adsorbed onto a nitrocellulose membrane (Hybond-ECL; manufactured by Amersham Pharmacia Biotech Inc.) using HorizBlot (manufactured by Atto Co.). For the western blotting, anti-glucocorticoid receptor antibody (manufactured by Santa Cruz), anti-Akt antibody (manufactured by Cell Signaling Technology), anti-cyclin dependent kinase 4 antibody (manufactured by Calbiochem) or anti-β-actin antibody (manufactured by Sigma) was used as a primer antibody, and horseradish peroxidase-labeled anti-rabbit IgG antibody (manufactured by Cell Signaling Technology) or horseradish peroxidase-labeled anti-mouse IgG antibody (manufactured by Kirkegaard & Perry Laboratories) was used as a secondary antibody. β-Actin was used to verify the step of adsorbing the proteins onto the nitrocellulose membrane.

(3) Results of Measurement

Compound A as the test compound did not affect the intracellular protein level of the Hsp90 client protein such as glucocorticoid receptor, Akt, cyclin dependent kinase 4, etc. at concentrations of 10 μM or less.

Figure 5:
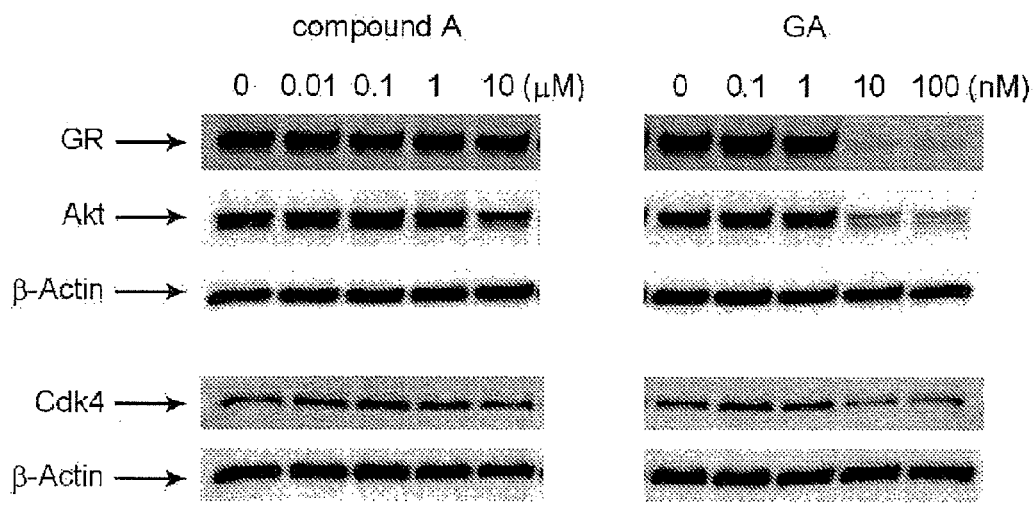
FIG. 5 is western blots showing the results of comparing the Hsp90 client protein degradation activity of the test compound (Compound A) and the reference compound (GA).

On the other hand, the reference compound GA decreased the intracellular protein level of glucocorticoid receptor, Akt, cyclin dependent kinase 4, etc. at concentrations of 10 μM or less. The effect was especially remarkable with glucocorticoid receptor and Akt (FIG. 5). The client protein degradation-inducing activity of Compound A is less than 1/1000, as compared to GA.

According to this step, it was shown that the test compound having no or minimized Hsp90 client protein degradation-inducing activity can be screened.

Example 6

Verification of Cell Protecting Activity

The cell protecting activity of Compound A and GA was verified according to the following procedures.

Figure 6:
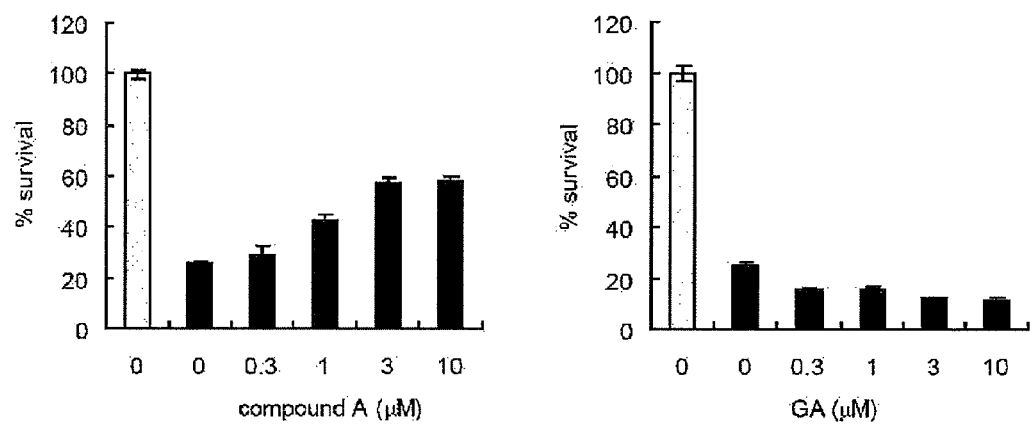
FIG. 6 is graphs showing the cell protecting activity of the compound (compound A) and the reference compound (GA).

First, human normal articular chondrocytes were suspended to $4 \times 10^4$ cells/ml in a growth medium for articular chondrocytes. The cell culture was inoculated into a 96-well plate, followed by incubation at 37° C. for a day under 5% $CO_2$. The medium was exchanged to a 1:1 mixture of Dulbecco's modified Eagle's medium/Ham F12 medium. The test compound and 10 ng/ml of IL-113 were added to the medium, followed by further incubation at 37° C. for a day under 5% $CO_2$. Next, 110 μM nitrogen monoxide-releasing reagent, i.e., (±)-(E)-4-ethyl-2-[(E)-hydroximino]-5-nitro-3-hexenamide (NOR3; manufactured by Dojindo) was added and the mixture was incubated for a day to induce apoptosis of the cells. After completion of the incubation, a viability of the cells was determined using 3-(4,5-dimethylthiazol-2-yl)-2,5-diphenyltetrazorium bromide (MTT; manufactured by Dojindo). As a result, Compound A dose-dependently suppressed the apoptosis, whereas GA decreased the cell viability (FIG. 6). Compound A was verified to have an excellent cell protecting activity.

(Verification of Cytotoxicity)

The cytotoxicity of Compound A and GA was verified according to the following procedures.

Figure 7:
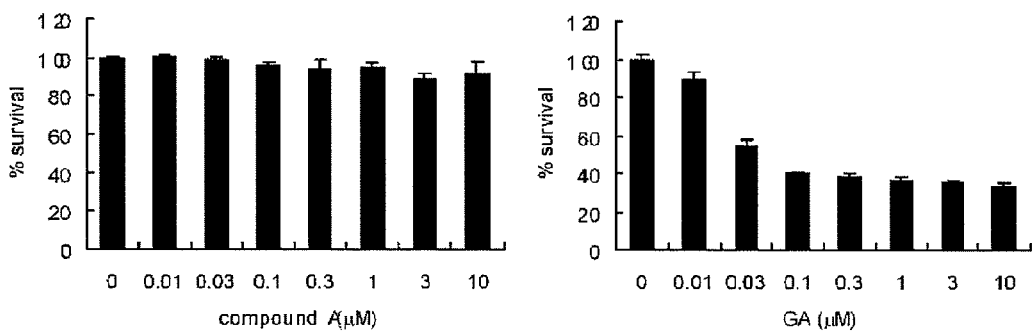
FIG. 7 is graphs showing the cytotoxicity of the compound (compound A) and the reference compound (GA).

First, human normal articular chondrocytes were suspended to $5 \times 10^4$ cells/ml in a growth medium for articular chondrocytes. The cell culture was inoculated into a 96-well plate, followed by incubation at 37° C. for a day under 5% $CO_2$. The test compound was added to the medium, followed by incubation at 37° C. for further 2 days under 5% $CO_2$. After completion of the incubation, the cell viability was determined using (2-(2-methoxy-4-nitrophenyl)-3-(4-nitrophenyl)-5-(2,4-disulfophenyl)-2H-tetrazolium, monosodium salt (WST-8; manufactured by Dojindo). As a result, Compound A did not affect the cell viability at concentrations of 10 μM or less, whereas GA greatly decreased the cell viability at concentrations of 30 nM or higher (FIG. 7). The cytotoxicity of Compound A would be 1/300 or less than that of GA.

It was confirmed from the foregoing results that Compound A is an excellent cell protecting agent having a minimized cytotoxicity.

(Results of Screening)

According to the steps (1), (2) and (3), it was verified that compound A has the properties of "the cell protecting agent showing the Hsp90 binding activity and the heat shock protein expression-inducing activity but having no Hsp90 client protein degradation-promoting activity" or "the cell protecting agent showing the Hsp90 binding activity and the Hsp90/HSF-1 complex disrupting activity but having no Hsp90 client protein degradation-promoting activity" and further verified that Compound A has a minimized cytotoxicity.

With the screening method of the present invention, it is represented that "the cell protecting agent showing the Hsp90 binding activity and the heat shock protein expression-inducing activity but having no Hsp90 client protein degradation-promoting activity" or "the cell protecting agent showing the Hsp90 binding activity and the Hsp90/HSF-1 complex disrupting activity but having no Hsp90 client protein degradation-promoting activity" is obtained. The screening method of the present invention can be used to search for excellent cell protecting agents.

INDUSTRIAL APPLICABILITY

The present invention is useful as the cell protecting agent showing the Hsp90 binding activity and the heat shock protein expression-inducing activity but having no Hsp90 client protein degradation-promoting activity and also useful for the process and kit, etc. for screening such a cell protecting agent.

The invention claimed is:

1. A method for screening for a cell protecting agent, which comprises:
    (1) measuring whether a test compound modulates the binding of Hsp90 to an imidazothiazine derivative,
    (2) contacting said test compound with a human normal articular chondrocyte or an extract of said cell, and measuring either
        i) the amount of expression of Hsp40, Hsp70, or Hsp90 induced by the test compound or
        ii) the degree to which the test compound disrupts an Hsp90/HSF-1 complex,
    (3) contacting said test compound with a human normal articular chondrocyte or an extract of said cell and measuring the amount of degradation of an Hsp90 client protein induced by the test compound, wherein the Hsp90 client protein is one or more proteins selected from the group consisting of a glucocorticoid receptor, Akt, and cycline dependent kinase 4, and
    (4) selecting a test compound that modulates binding of Hsp90 to the imidazothiazine derivative in step (1), and either induces expression of an Hsp in step (2)(i) or disrupts an Hsp90/HSF-1 complex in step (2)(ii), and does not degrade an Hsp90 client protein in step (3);
    wherein the imidazothiazine derivative is N-[(1Z)-5,6-dimethyl-3-oxo-8-[(4,4,5,5,5-pentafluoropentyl)sulfanyl]-2,3-dihydro-1H-imidazo[5,1-c][1,4]thiazin-1-ylidene]-4-methylbenzenesulfonamide or 5-[[(1Z)-5,6-dimethyl-3-oxo-1-([[4-(trifluoromethyl)phenyl]sulfonyl]imino-)-2,3-dihydro-1H-imidazo[5,1-c][1,4]thiazin-8-yl]sulfanyl]pentanoic acid; and
    wherein the Hsp90 or the imidazothiazine derivative is bound to a carrier selected from the group consisting of insoluble polysaccharides of agarose, dextran and cellulose, synthetic resins of polystyrene, polyacrylamide and silicone, and glass.

2. The screening method according to claim 1, wherein step (3) further comprises measuring the degree to which the test compound inhibits binding between Hsp90 and the Hsp90 client protein.

3. The screening method according to claim 1, wherein the step (3) comprises measuring and comparing (i) the level of the Hsp90 client protein in the cell in the absence of the test compound and (ii) the level of the Hsp90 client protein in the cell in the presence of the test compound.

4. The screening method according to claim 3, wherein the level of the Hsp90 client protein is measured by western blotting using an antibody against the Hsp90 client protein.

5. The screening method according to claim 1, wherein the cell protecting agent is an agent for the prevention/treatment of heart disease, neurological disease, brain disease, bone/joint disease, renal disease, liver disease or skin disease.

* * * * *